(12) United States Patent
Ogura

(10) Patent No.: US 11,673,927 B2
(45) Date of Patent: Jun. 13, 2023

(54) ANTITUMOR AGENT TARGETING HGF-REGULATED TYROSINE KINASE SUBSTRATE (HGS)

(71) Applicant: TOKYO METROPOLITAN INSTITUTE OF MEDICAL SCIENCE, Tokyo (JP)

(72) Inventor: Kiyoshi Ogura, Tokyo (JP)

(73) Assignee: TOKYO METROPOLITAN INSTITUTE OF MEDICAL SCIENCE, Tokyo (JP)

(*) Notice: Subject to any disclaimer, the term of this patent is extended or adjusted under 35 U.S.C. 154(b) by 0 days.

(21) Appl. No.: 17/271,088

(22) PCT Filed: Aug. 28, 2019

(86) PCT No.: PCT/JP2019/033654
§ 371 (c)(1),
(2) Date: Feb. 24, 2021

(87) PCT Pub. No.: WO2020/045479
PCT Pub. Date: Mar. 5, 2020

(65) Prior Publication Data
US 2022/0144905 A1    May 12, 2022

(30) Foreign Application Priority Data
Aug. 29, 2018 (JP) .............................. JP2018-160501

(51) Int. Cl.
| | |
|---|---|
| *A61K 38/08* | (2019.01) |
| *A61K 38/10* | (2006.01) |
| *A61K 38/00* | (2006.01) |
| *A61P 35/00* | (2006.01) |
| *A61P 35/04* | (2006.01) |
| *C07K 7/06* | (2006.01) |
| *C07K 7/08* | (2006.01) |
| *C07K 14/47* | (2006.01) |

(52) U.S. Cl.
CPC .......... *C07K 14/4703* (2013.01); *A61P 35/04* (2018.01); *A61K 38/00* (2013.01)

(58) Field of Classification Search
CPC ........ A61K 38/00; A61K 38/08; A61K 38/10; A61P 35/00; A61P 35/04; C07K 14/4703; C07K 14/47; C07K 7/06; C07K 7/08
See application file for complete search history.

(56) References Cited

U.S. PATENT DOCUMENTS

| | | | | |
|---|---|---|---|---|
| 5,595,756 A * | 1/1997 | Bally | ................ | A61K 9/1272 264/4.1 |
| 2013/0190240 A1* | 7/2013 | Ogura | .................. | C07K 7/06 514/19.3 |
| 2017/0290882 A1* | 10/2017 | Andronova | ........ | A61K 31/7068 |
| 2017/0360955 A1* | 12/2017 | Janssen | ............. | C07K 16/2863 |

FOREIGN PATENT DOCUMENTS

| | | |
|---|---|---|
| EP | 2 586 453 A1 | 5/2013 |
| WO | WO 2011/162419 A1 | 12/2011 |
| WO | WO 2013/143026 A1 | 10/2013 |
| WO | WO 2016/081947 A2 | 5/2016 |

OTHER PUBLICATIONS

Gravanis et al., "The changing world of cancer drug development: the regulatory bodies' perspective," Chin. Clin. Oncol., 2014, 3(2); 22, pp. 1-5. (Year: 2014).*
Hait WN., "Anticancerdrug development: the grand challenges," Nature Reviews, Apr. 2010, 9: 253-254. (Year: 2010).*
Neidle, Stephen, ed, "Cancer Drug Design and Discovery," Elsevier/Academic Press, 2008, pp. 427-431. (Year: 2008).*
Gura T., "Systems for Identifying New Drugs Are Often Faulty," Science, 1997, 278: 1041-1042. (Year: 1997).*
Auerbach et al., "Angiogenesis assays: Problems and pitfalls," Cancer and Metastasis Reviews, 2000, 19: 167-172. (Year: 2000).*
Jain RK., "Barriers to Drug Delivery in Solid Tumors," Scientific American, 1994, pp. 58-65. (Year: 1994).*
Sporn et al., "Chemoprevention of cancer," Carcinogenesis, 2000, 21(3): 525-530. (Year: 2000).*
International Search Report issued in PCT/JP2019/033654 (PCT/ISA/210), dated Nov. 12, 2019.
Ogura et al., "Comprehensive search of HGS/C oligopeptides that suppress tumor growth and metastasis", Programs and abstracts of Annual meeting of the Japanese Association for Metastasis Research, vol. 26, 2017, p. 111 (Total No. Pgs. 3).
Ogura et al., "Tumor growth suppression with GEF-1/Hgs as a molecular target-2, Suppression of cancer properties by GEF/C component oligopeptides", Programs and abstracts of annual meeting of the Japanese Association for Metastasis Research, vol. 21, 2012, p. 92 (Total No. Pgs. 3).
Written Opinion of the International Searching Authority issued in PCT/JP2019/033654 (PCT/ISA/237), dated Nov. 12, 2019.
Extended European Search Report for European Patent Application No. 19853934.8, dated Jun. 28, 2022.
Ogura et al., "Tumor growth suppressive oligopeptides which derive from HGS/C protein," Cancer Science, vol. 109, Issue S2, Dec. 2018, p. 1008.

* cited by examiner

*Primary Examiner* — Julie Ha
(74) *Attorney, Agent, or Firm* — Birch, Stewart, Kolasch & Birch, LLP

(57) ABSTRACT

The present invention aims to provide a peptide of the C region of HGS and an antitumor agent comprising the same having a higher tumor growth inhibitory effect as compared with conventional techniques. An antitumor agent comprising a peptide comprising at least 10 consecutive amino acid residues of the amino acid sequence of the C region of HGS is described.

6 Claims, 6 Drawing Sheets

Specification includes a Sequence Listing.

[Figure 1]
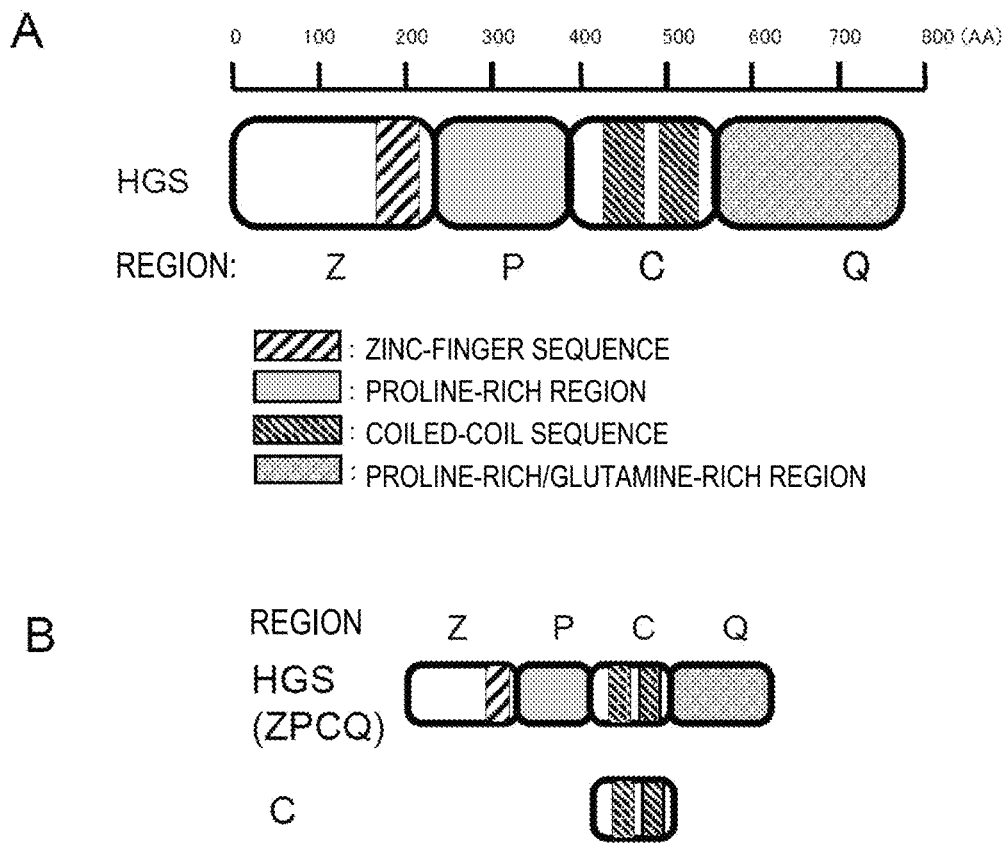
[Figure 2A]
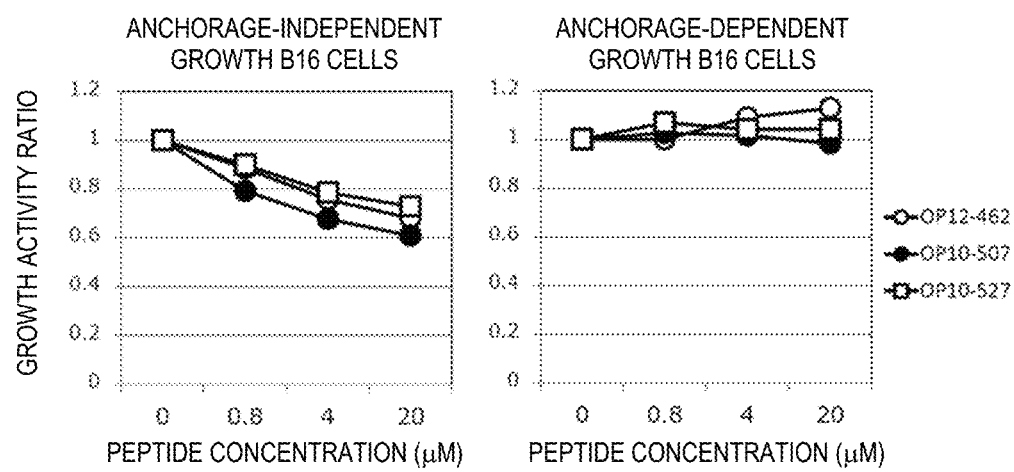

[Figure 2B]
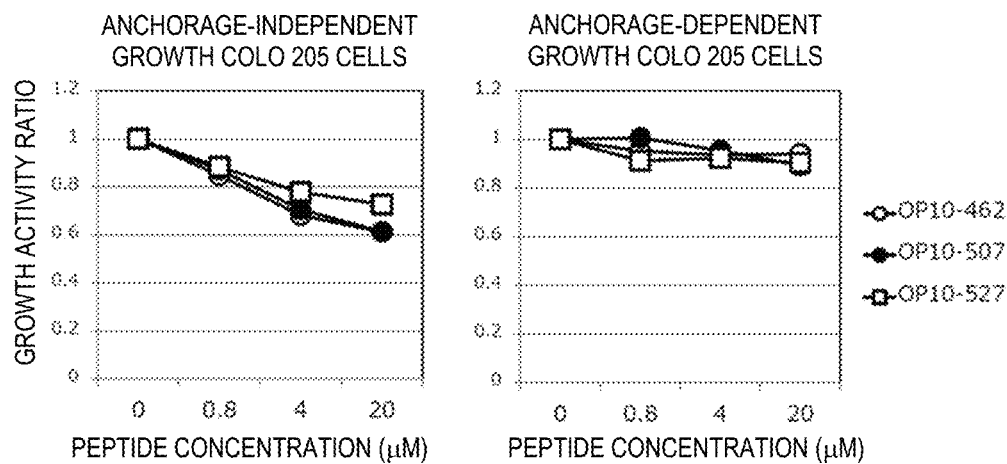
[Figure 3A]
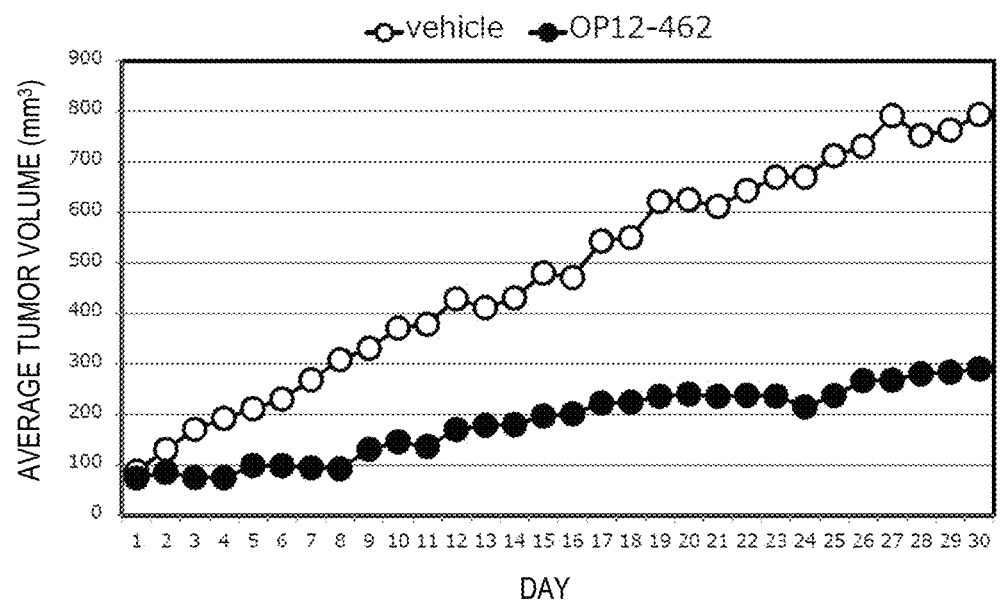

[Figure 3B]
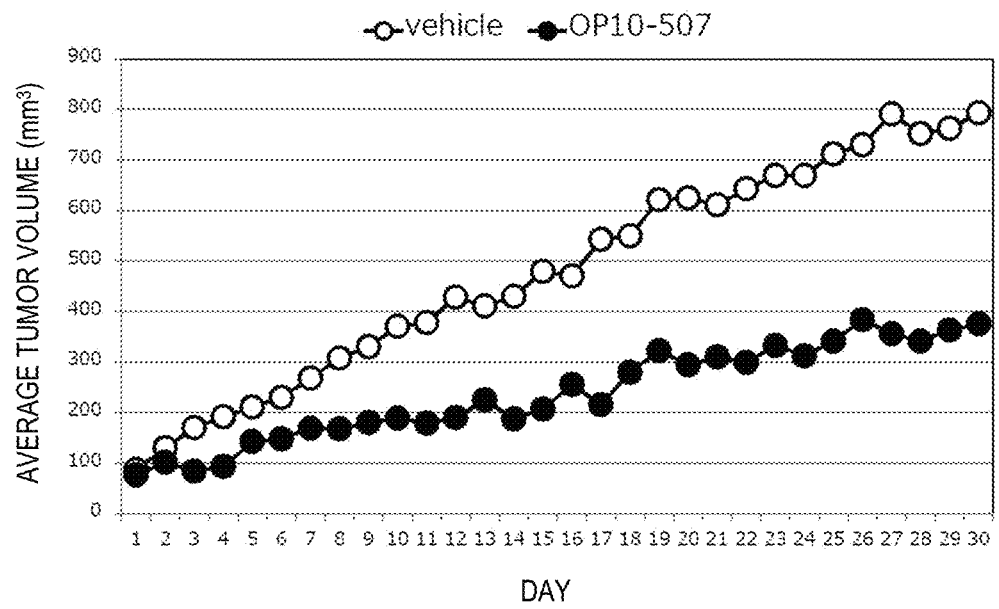
[Figure 3C]
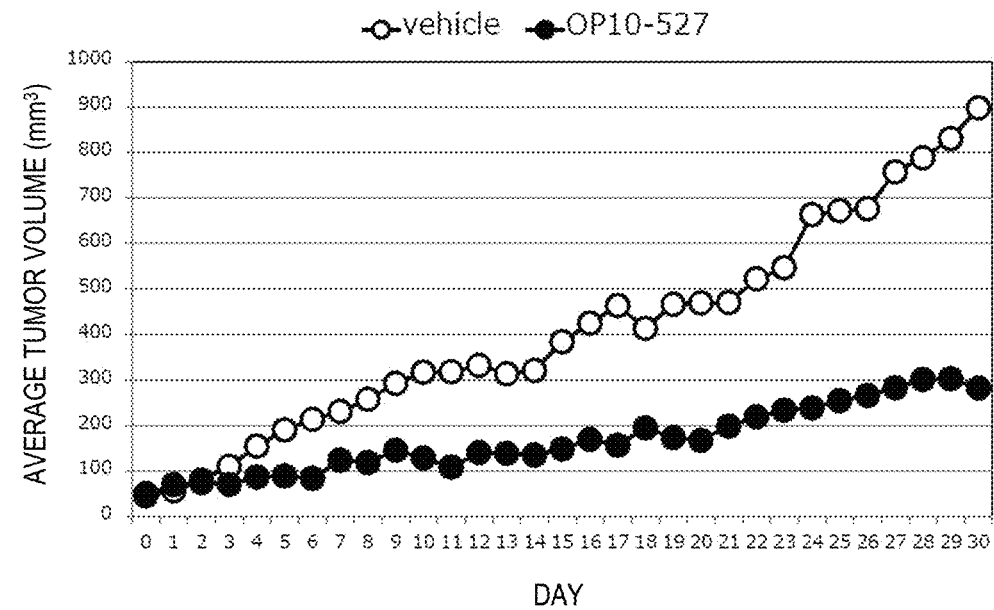

[Figure 4]
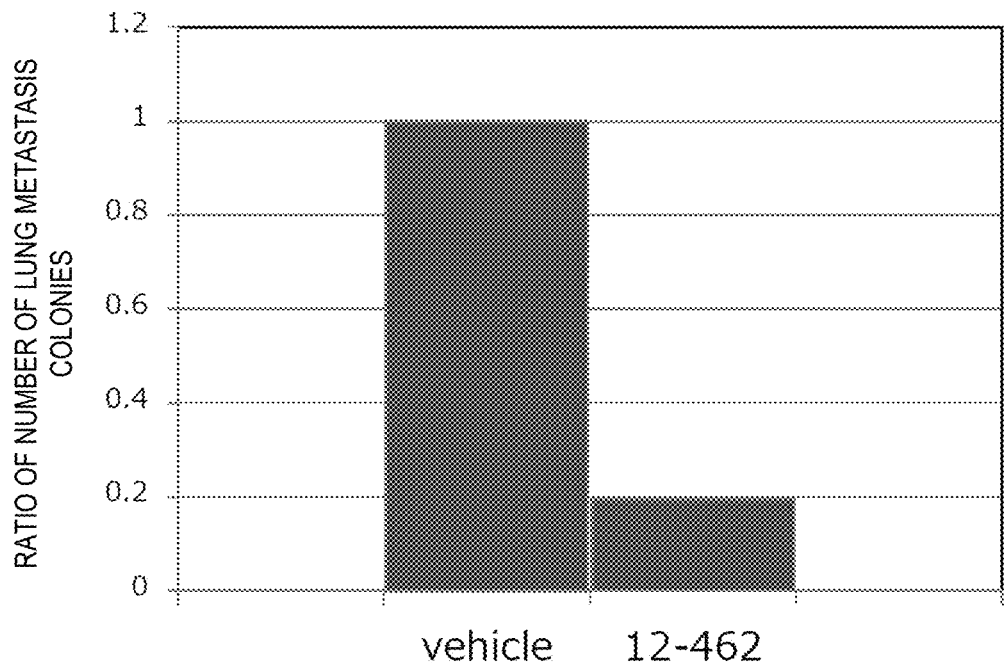
[Figure 5]
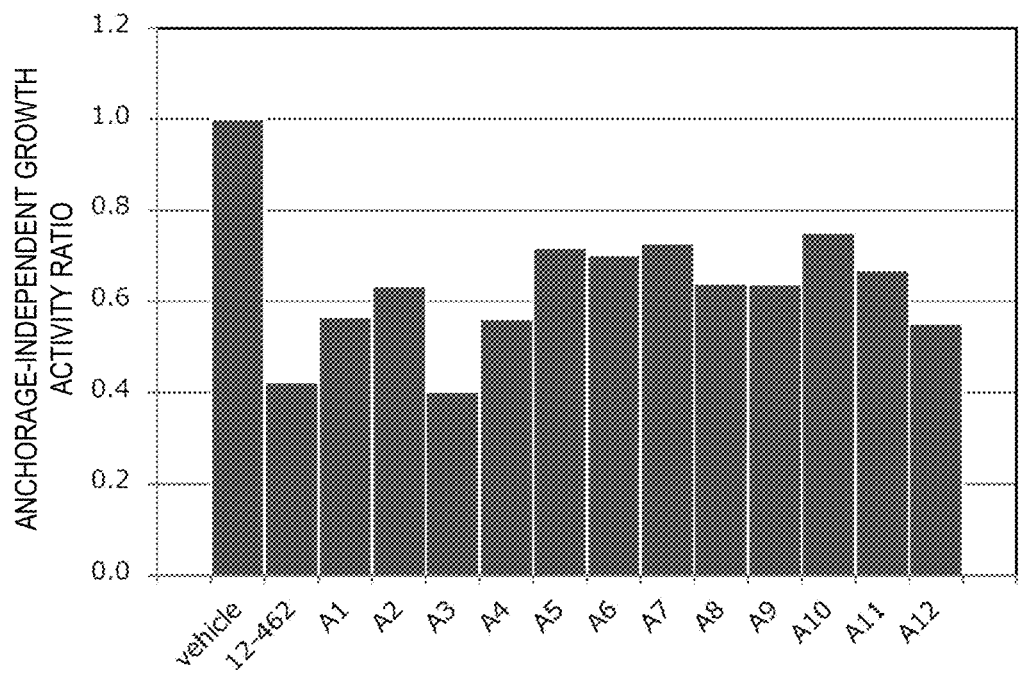

[Figure 6A]
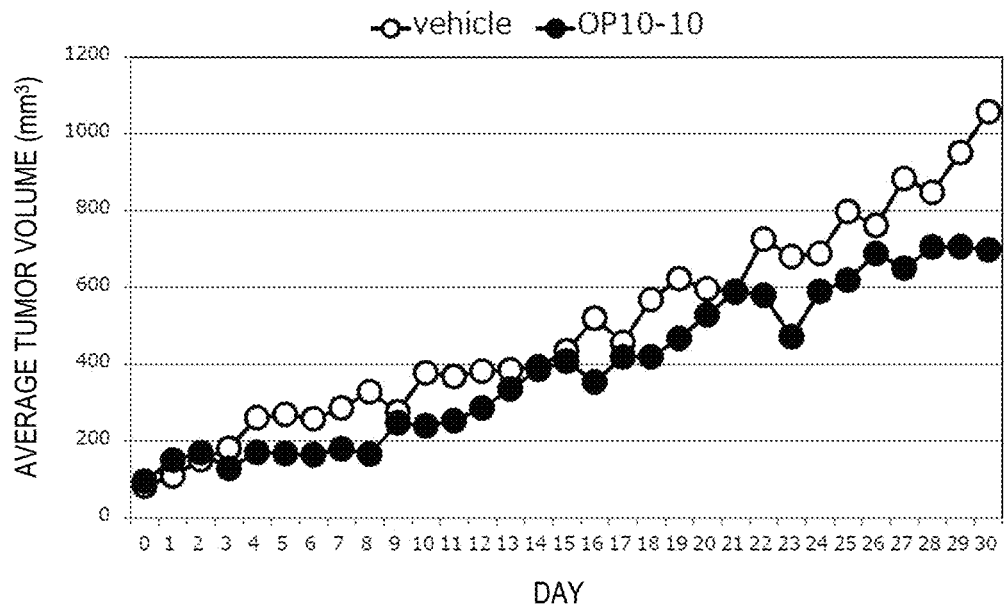
[Figure 6B]
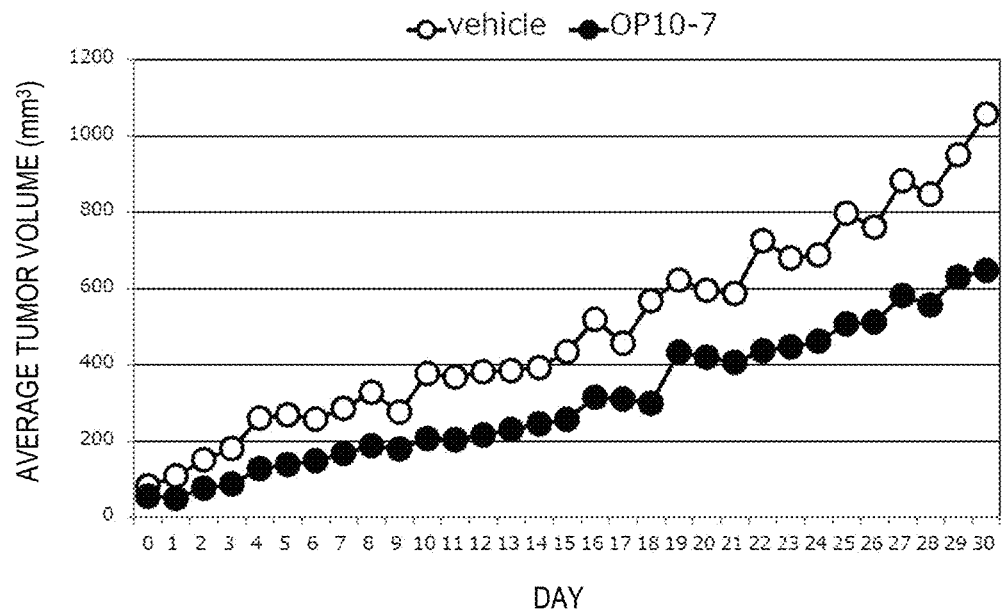

[Figure 6C]
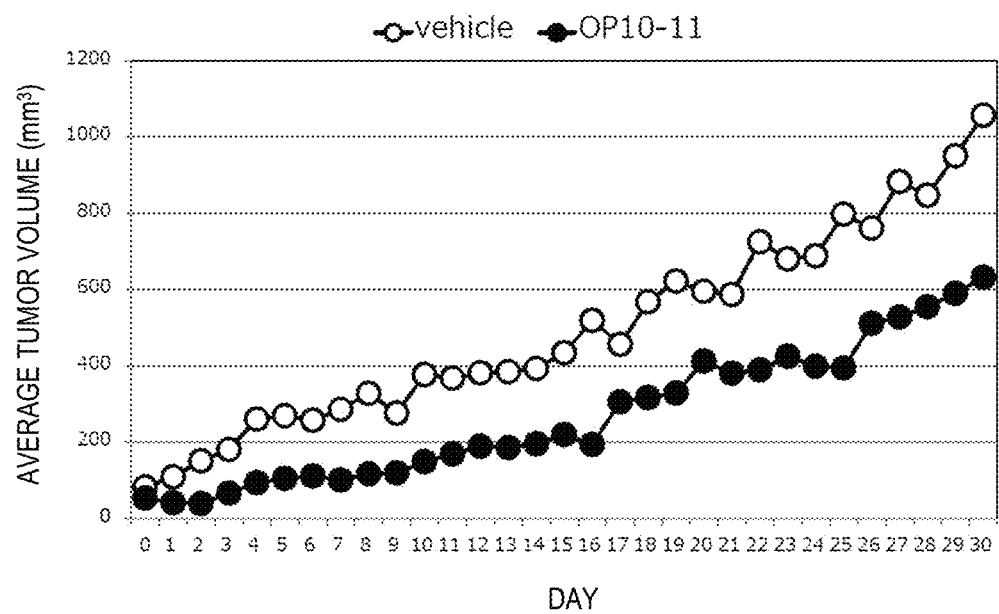

SEQUENCE LISTING

<160> NUMBER OF SEQ ID NOS: 96

<210> SEQ ID NO 1
<211> LENGTH: 2827
<212> TYPE: DNA
<213> ORGANISM: Rattus norvegicus
<220> FEATURE:
<221> NAME/KEY: CDS
<222> LOCATION: (21)..(2336)

<400> SEQUENCE: 1

```
cggtccggag tggggtcgcc atg ggg cga ggc agc ggc acc ttc gag cgt ctc    53
                     Met Gly Arg Gly Ser Gly Thr Phe Glu Arg Leu
                      1               5                  10 cta gac aaa gcc acc agc cag ctt cta ttg gag aca gac tgg gag tcc    101
Leu Asp Lys Ala Thr Ser Gln Leu Leu Leu Glu Thr Asp Trp Glu Ser
             15                  20                  25 att cta cag atc tgc gac ctg atc cgt cag ggg gac aca caa gca aaa    149
Ile Leu Gln Ile Cys Asp Leu Ile Arg Gln Gly Asp Thr Gln Ala Lys
         30                  35                  40 tat gct gta aac tcc atc aag aag aag gtc aat gat aag aac cca cat    197
Tyr Ala Val Asn Ser Ile Lys Lys Lys Val Asn Asp Lys Asn Pro His
 45                  50                  55 gtg gct ttg tat gct ctg gag gtg atg gag tct gtg gta aag aac tgt    245
Val Ala Leu Tyr Ala Leu Glu Val Met Glu Ser Val Val Lys Asn Cys
 60                  65                  70                  75 ggc cag aca gtc cat gat gaa gtg gcc aac aaa cag acc atg gaa gaa    293
Gly Gln Thr Val His Asp Glu Val Ala Asn Lys Gln Thr Met Glu Glu
             80                  85                  90 ctg aag gag ctg ctg aag agg caa gtg gaa gtt aat gtt cgg aac aag    341
Leu Lys Glu Leu Leu Lys Arg Gln Val Glu Val Asn Val Arg Asn Lys
             95                 100                 105 atc ttg tac ctg atc cag gcc tgg gca cat gcg ttc cgg aat gaa ccc    389
Ile Leu Tyr Leu Ile Gln Ala Trp Ala His Ala Phe Arg Asn Glu Pro
        110                 115                 120 aag tac aag gtg gtc cag gac aca tac cag atc atg aag gta gaa gga    437
Lys Tyr Lys Val Val Gln Asp Thr Tyr Gln Ile Met Lys Val Glu Gly
125                 130                 135 cat gtc ttc cct gag ttt aag gag agt gac gcc atg ttt gct gct gaa    485
His Val Phe Pro Glu Phe Lys Glu Ser Asp Ala Met Phe Ala Ala Glu
140                 145                 150                 155 aga gcc cct gac tgg gtg gat gct gag gag tgc cat cgg tgc aga gta    533
Arg Ala Pro Asp Trp Val Asp Ala Glu Glu Cys His Arg Cys Arg Val
                160                 165                 170 cag ttt gga gtg gtg acc cgc aag cat cac tgc cga gcg tgt ggg cag    581
Gln Phe Gly Val Val Thr Arg Lys His His Cys Arg Ala Cys Gly Gln
            175                 180                 185 atc ttt tgt ggc aag tgt tcc tcc aag tac tcc acc atc ccc aag ttc    629
Ile Phe Cys Gly Lys Cys Ser Ser Lys Tyr Ser Thr Ile Pro Lys Phe
        190                 195                 200 ggc att gag aag gaa gtg cgc gtg tgt gag ccc tgc tat gag cag ctg    677
Gly Ile Glu Lys Glu Val Arg Val Cys Glu Pro Cys Tyr Glu Gln Leu
    205                 210                 215 aac aag aag gca gaa ggg aaa gct gcc tct acc act gag ctg ccc cca    725
Asn Lys Lys Ala Glu Gly Lys Ala Ala Ser Thr Thr Glu Leu Pro Pro
220                 225                 230                 235 gag tac ctg acc agc ccc ctg tca cag cag tct cag ctg ccc cca aag    773
Glu Tyr Leu Thr Ser Pro Leu Ser Gln Gln Ser Gln Leu Pro Pro Lys
                240                 245                 250 cgg gat gag aca gca ctg caa gaa gag gag gag cta cag ctg gcg ctg    821
Arg Asp Glu Thr Ala Leu Gln Glu Glu Glu Glu Leu Gln Leu Ala Leu
            255                 260                 265 gcc cta tca cag tca gag gct gag gag aag gaa agg atg aga cag aag    869
Ala Leu Ser Gln Ser Glu Ala Glu Glu Lys Glu Arg Met Arg Gln Lys
        270                 275                 280 tca aca tac aca gcg cat cca aag tca gag cct gcg ccc ttg gct tcc    917
Ser Thr Tyr Thr Ala His Pro Lys Ser Glu Pro Ala Pro Leu Ala Ser
285                 290                 295
```

-continued

| | | |
|---|---|---|
| tct gca ccc cca gct ggt agc ctg tac tcc tcg cct gtg aac tca tca<br>Ser Ala Pro Pro Ala Gly Ser Leu Tyr Ser Ser Pro Val Asn Ser Ser<br>300                              305                        310                      315 | 965 | |
| gca cct ctg gct gag gac atc gac cct gag ctt gca aga tac ctc aac<br>Ala Pro Leu Ala Glu Asp Ile Asp Pro Glu Leu Ala Arg Tyr Leu Asn<br>                  320                        325                        330 | 1013 | |
| cgg aac tac tgg gag aag aaa cag gaa gaa gct cgg aag agc ccc aca<br>Arg Asn Tyr Trp Glu Lys Lys Gln Glu Glu Ala Arg Lys Ser Pro Thr<br>                        335                        340                        345 | 1061 | |
| cca tct gca cct gtg ccc ctg acc gag cca gct gcc cag ccc gga gaa<br>Pro Ser Ala Pro Val Pro Leu Thr Glu Pro Ala Ala Gln Pro Gly Glu<br>                  350                        355                        360 | 1109 | |
| gga cat aca gcc ccc aac agc atg gta gag gcc cct ctt cca gag aca<br>Gly His Thr Ala Pro Asn Ser Met Val Glu Ala Pro Leu Pro Glu Thr<br>      365                        370                        375 | 1157 | |
| gac tct cag ccc ata act tcc tgc agt ggc ccc ttt agt gag cag tac<br>Asp Ser Gln Pro Ile Thr Ser Cys Ser Gly Pro Phe Ser Glu Gln Tyr<br>380                              385                        390                      395 | 1205 | |
| cag aac gcg gag tcg gag gag agc cac gag cag ttc ctc aag gcc ctg<br>Gln Asn Ala Glu Ser Glu Glu Ser His Glu Gln Phe Leu Lys Ala Leu<br>                    400                        405                        410 | 1253 | |
| cag aat gca gtc agc act ttt gtc aac cgc atg aag agc aac cac atg<br>Gln Asn Ala Val Ser Thr Phe Val Asn Arg Met Lys Ser Asn His Met<br>                415                        420                        425 | 1301 | |
| agg ggc cgc agt atc acc aat gac tcg gct gtg ctg tcc ctc ttc cag<br>Arg Gly Arg Ser Ile Thr Asn Asp Ser Ala Val Leu Ser Leu Phe Gln<br>            430                        435                        440 | 1349 | |
| tcc atc aat agc aca cac cca cag ctg ctc gag ctg ctc aac cgg ctg<br>Ser Ile Asn Ser Thr His Pro Gln Leu Leu Glu Leu Leu Asn Arg Leu<br>445                              450                        455 | 1397 | |
| gat gag cgc agg ctg tac tac gag ggg ctt cag gac aag ctg gca cag<br>Asp Glu Arg Arg Leu Tyr Tyr Glu Gly Leu Gln Asp Lys Leu Ala Gln<br>460                              465                        470                      475 | 1445 | |
| ata cgt gat gcc cga ggg gcc ctg agt gcc ctg cgt gaa gag cac agg<br>Ile Arg Asp Ala Arg Gly Ala Leu Ser Ala Leu Arg Glu Glu His Arg<br>                  480                        485                        490 | 1493 | |
| gag aag ctg cgc cgg gca gct gag gag gcg gag cgt caa cgt cag atc<br>Glu Lys Leu Arg Arg Ala Ala Glu Glu Ala Glu Arg Gln Arg Gln Ile<br>                495                        500                        505 | 1541 | |
| cag ctg gca cag aag ctg gag atc atg aga caa aag aag cag gag tat<br>Gln Leu Ala Gln Lys Leu Glu Ile Met Arg Gln Lys Lys Gln Glu Tyr<br>            510                        515                        520 | 1589 | |
| ctg gag gtg cag aga cag cta gct atc cag cgt ctg cag gaa cag gag<br>Leu Glu Val Gln Arg Gln Leu Ala Ile Gln Arg Leu Gln Glu Gln Glu<br>525                              530                        535 | 1637 | |
| aag gaa cgg cag atg cgc ctg gag caa cag aag cag act gtc cag atg<br>Lys Glu Arg Gln Met Arg Leu Glu Gln Gln Lys Gln Thr Val Gln Met<br>540                              545                        550                      555 | 1685 | |
| cgt gcc cag atg cct gtc ttc ccc ttg cct tat gcc cag ctc cag gct<br>Arg Ala Gln Met Pro Val Phe Pro Leu Pro Tyr Ala Gln Leu Gln Ala<br>                  560                        565                        570 | 1733 | |
| atg ccc aca gct ggg ggt gta ctc tac cag ccc tca ggc cca acc agc<br>Met Pro Thr Ala Gly Gly Val Leu Tyr Gln Pro Ser Gly Pro Thr Ser<br>                        575                        580                        585 | 1781 | |
| ttt cct ggc acc ttt agc cca gca ggc tca gta gag ggc tct ccg atg<br>Phe Pro Gly Thr Phe Ser Pro Ala Gly Ser Val Glu Gly Ser Pro Met<br>              590                        595                        600 | 1829 | |
| cat ggt gtg tat atg agc cag cca gcc cca gcc act ggc ccc tac ccc<br>His Gly Val Tyr Met Ser Gln Pro Ala Pro Ala Thr Gly Pro Tyr Pro<br>      605                        610                        615 | 1877 | |

-continued

| | | | | | | | | | | | | | | | | |
|---|---|---|---|---|---|---|---|---|---|---|---|---|---|---|---|---|
| agc | atg | cct | ggc | acc | aca | gca | gat | ccc | agc | atg | gtc | agc | gcc | tac | atg | 1925 |
| Ser | Met | Pro | Gly | Thr | Thr | Ala | Asp | Pro | Ser | Met | Val | Ser | Ala | Tyr | Met | |
| 620 | | | | | 625 | | | | | 630 | | | | | 635 | |
| tac | cca | gca | ggt | gcc | cct | ggg | gca | cag | gca | gcc | cct | cag | gcc | cag | gcc | 1973 |
| Tyr | Pro | Ala | Gly | Ala | Pro | Gly | Ala | Gln | Ala | Ala | Pro | Gln | Ala | Gln | Ala | |
| | | | | 640 | | | | | 645 | | | | | 650 | | |
| ggg | ccc | acc | acc | aac | cct | gcc | tac | tcc | tcg | tac | cag | cct | act | cca | acc | 2021 |
| Gly | Pro | Thr | Thr | Asn | Pro | Ala | Tyr | Ser | Ser | Tyr | Gln | Pro | Thr | Pro | Thr | |
| | | | 655 | | | | | 660 | | | | | 665 | | | |
| cca | ggc | tac | cag | gcc | cca | cag | agc | ctc | cca | gcc | atc | tcc | cag | cct | cca | 2069 |
| Pro | Gly | Tyr | Gln | Ala | Pro | Gln | Ser | Leu | Pro | Ala | Ile | Ser | Gln | Pro | Pro | |
| | | 670 | | | | | 675 | | | | | 680 | | | | |
| cag | acc | agc | aac | att | ggc | tac | atg | ggg | agc | cag | cca | atg | tcc | atg | ggc | 2117 |
| Gln | Thr | Ser | Asn | Ile | Gly | Tyr | Met | Gly | Ser | Gln | Pro | Met | Ser | Met | Gly | |
| | 685 | | | | | 690 | | | | | 695 | | | | | |
| tac | cag | cca | tac | aac | atg | cag | aat | ctc | atg | acc | acc | ctt | cca | ggc | cag | 2165 |
| Tyr | Gln | Pro | Tyr | Asn | Met | Gln | Asn | Leu | Met | Thr | Thr | Leu | Pro | Gly | Gln | |
| 700 | | | | | 705 | | | | | 710 | | | | | 715 | |
| gat | gcg | tct | ctg | cca | gcc | cag | cag | ccc | tac | atc | aca | ggg | cag | cag | ccc | 2213 |
| Asp | Ala | Ser | Leu | Pro | Ala | Gln | Gln | Pro | Tyr | Ile | Thr | Gly | Gln | Gln | Pro | |
| | | | | 720 | | | | | 725 | | | | | 730 | | |
| atg | tac | cag | cag | atg | gca | ccc | agc | act | ggc | cct | ccc | cag | cag | cag | ccc | 2261 |
| Met | Tyr | Gln | Gln | Met | Ala | Pro | Ser | Thr | Gly | Pro | Pro | Gln | Gln | Gln | Pro | |
| | | | 735 | | | | | 740 | | | | | 745 | | | |
| cct | gtg | gcc | caa | ccg | cca | cct | aca | cag | gga | ccg | cca | gca | cag | ggc | aat | 2309 |
| Pro | Val | Ala | Gln | Pro | Pro | Pro | Thr | Gln | Gly | Pro | Pro | Ala | Gln | Gly | Asn | |
| | | 750 | | | | | 755 | | | | | 760 | | | | |
| gag | acc | cag | ctc | atc | tcc | ttc | gac | tga | ccttgagtct | | | ggcgctcacc | | | | 2356 |
| Glu | Thr | Gln | Leu | Ile | Ser | Phe | Asp | | | | | | | | | |
| | 765 | | | | | 770 | | | | | | | | | | |

| | |
|---|---|
| atccagagta acactacagt tctccagaaa ccactt atat gtctaactag ccatttcctc | 2416 |
| ccattactgc cctgtagtgt cccttctgtg agcaagg ggt gggccttcac ccttggccct | 2476 |
| cctccctgtc ctcagtggtc tggctcctgt cactggt tcc ctgctttggt cctgatgcag | 2536 |
| tccaaccttc ccgggactgg gactctgcag acaagt agg accttttctg gagaatgccc | 2596 |
| agctgtgtcg gggcctgcca gaggtgactg ctgtggg gat ggttagcctg gcccagagtc | 2656 |
| cgatgtgaac tgtgtggtgt ccaggcatgg ccctggt acc cagaagaacg atgtgaccca | 2716 |
| tgcacagcaa ggtagaagtg ttcaggcatc tctgtct ccc ctactccttg gatgtcatct | 2776 |
| ctccagtgca gaacagtgaa ataaaatgt attcaaaaaa aaaaaaaaa a | 2827 |

<210> SEQ ID NO 2
<211> LENGTH: 771
<212> TYPE: PRT
<213> ORGANISM: Rattus norvegicus

<400> SEQUENCE: 2

Met Gly Arg Gly Ser Gly Thr Phe Glu Arg Leu Leu Asp Lys Ala Thr
1               5                   10                  15

Ser Gln Leu Leu Leu Glu Thr Asp Trp Glu Ser Ile Leu Gln Ile Cys
            20                  25                  30

Asp Leu Ile Arg Gln Gly Asp Thr Gln Ala Lys Tyr Ala Val Asn Ser
        35                  40                  45

Ile Lys Lys Lys Val Asn Asp Lys Asn Pro His Val Ala Leu Tyr Ala
    50                  55                  60

Leu Glu Val Met Glu Ser Val Val Lys Asn Cys Gly Gln Thr Val His
65                  70                  75                  80

```
Asp Glu Val Ala Asn Lys Gln Thr Met Glu Glu Leu Lys Glu Leu Leu
                85                  90                  95

Lys Arg Gln Val Glu Val Asn Val Arg Asn Lys Ile Leu Tyr Leu Ile
            100                 105                 110

Gln Ala Trp Ala His Ala Phe Arg Asn Glu Pro Lys Tyr Lys Val Val
            115                 120                 125

Gln Asp Thr Tyr Gln Ile Met Lys Val Glu Gly His Val Phe Pro Glu
130                 135                 140

Phe Lys Glu Ser Asp Ala Met Phe Ala Ala Glu Arg Ala Pro Asp Trp
145                 150                 155                 160

Val Asp Ala Glu Glu Cys His Arg Cys Arg Val Gln Phe Gly Val Val
            165                 170                 175

Thr Arg Lys His His Cys Arg Ala Cys Gly Gln Ile Phe Cys Gly Lys
            180                 185                 190

Cys Ser Ser Lys Tyr Ser Thr Ile Pro Lys Phe Gly Ile Glu Lys Glu
            195                 200                 205

Val Arg Val Cys Glu Pro Cys Tyr Glu Gln Leu Asn Lys Lys Ala Glu
            210                 215                 220

Gly Lys Ala Ala Ser Thr Thr Glu Leu Pro Pro Glu Tyr Leu Thr Ser
225                 230                 235                 240

Pro Leu Ser Gln Gln Ser Gln Leu Pro Pro Lys Arg Asp Glu Thr Ala
            245                 250                 255

Leu Gln Glu Glu Glu Glu Leu Gln Leu Ala Leu Ala Leu Ser Gln Ser
            260                 265                 270

Glu Ala Glu Glu Lys Glu Arg Met Arg Gln Lys Ser Thr Tyr Thr Ala
            275                 280                 285

His Pro Lys Ser Glu Pro Ala Pro Leu Ala Ser Ser Ala Pro Pro Ala
            290                 295                 300

Gly Ser Leu Tyr Ser Ser Pro Val Asn Ser Ser Ala Pro Leu Ala Glu
305                 310                 315                 320

Asp Ile Asp Pro Glu Leu Ala Arg Tyr Leu Asn Arg Asn Tyr Trp Glu
            325                 330                 335

Lys Lys Gln Glu Glu Ala Arg Lys Ser Pro Thr Pro Ser Ala Pro Val
            340                 345                 350

Pro Leu Thr Glu Pro Ala Ala Gln Pro Gly Glu Gly His Thr Ala Pro
            355                 360                 365

Asn Ser Met Val Glu Ala Pro Leu Pro Glu Thr Asp Ser Gln Pro Ile
370                 375                 380

Thr Ser Cys Ser Gly Pro Phe Ser Glu Gln Tyr Gln Asn Ala Glu Ser
385                 390                 395                 400

Glu Glu Ser His Glu Gln Phe Leu Lys Ala Leu Gln Asn Ala Val Ser
            405                 410                 415

Thr Phe Val Asn Arg Met Lys Ser Asn His Met Arg Gly Arg Ser Ile
            420                 425                 430

Thr Asn Asp Ser Ala Val Leu Ser Leu Phe Gln Ser Ile Asn Ser Thr
            435                 440                 445

His Pro Gln Leu Leu Glu Leu Leu Asn Arg Leu Asp Glu Arg Arg Leu
            450                 455                 460

Tyr Tyr Glu Gly Leu Gln Asp Lys Leu Ala Gln Ile Arg Asp Ala Arg
465                 470                 475                 480

Gly Ala Leu Ser Ala Leu Arg Glu Glu His Arg Glu Lys Leu Arg Arg
            485                 490                 495
```

Ala Ala Glu Glu Ala Glu Arg Gln Arg Gln Ile Gln Leu Ala Gln Lys
                500                 505                 510

Leu Glu Ile Met Arg Gln Lys Lys Gln Glu Tyr Leu Glu Val Gln Arg
        515                 520                 525

Gln Leu Ala Ile Gln Arg Leu Gln Glu Gln Glu Lys Glu Arg Gln Met
    530                 535                 540

Arg Leu Glu Gln Gln Lys Gln Thr Val Gln Met Arg Ala Gln Met Pro
545                 550                 555                 560

Val Phe Pro Leu Pro Tyr Ala Gln Leu Gln Ala Met Pro Thr Ala Gly
                565                 570                 575

Gly Val Leu Tyr Gln Pro Ser Gly Pro Thr Ser Phe Pro Gly Thr Phe
            580                 585                 590

Ser Pro Ala Gly Ser Val Glu Gly Ser Pro Met His Gly Val Tyr Met
        595                 600                 605

Ser Gln Pro Ala Pro Ala Thr Gly Pro Tyr Pro Ser Met Pro Gly Thr
    610                 615                 620

Thr Ala Asp Pro Ser Met Val Ser Ala Tyr Met Tyr Pro Ala Gly Ala
625                 630                 635                 640

Pro Gly Ala Gln Ala Ala Pro Gln Ala Gln Ala Gly Pro Thr Thr Asn
                645                 650                 655

Pro Ala Tyr Ser Ser Tyr Gln Pro Thr Pro Thr Pro Gly Tyr Gln Ala
            660                 665                 670

Pro Gln Ser Leu Pro Ala Ile Ser Gln Pro Gln Thr Ser Asn Ile
        675                 680                 685

Gly Tyr Met Gly Ser Gln Pro Met Ser Met Gly Tyr Gln Pro Tyr Asn
    690                 695                 700

Met Gln Asn Leu Met Thr Thr Leu Pro Gly Gln Asp Ala Ser Leu Pro
705                 710                 715                 720

Ala Gln Gln Pro Tyr Ile Thr Gly Gln Gln Pro Met Tyr Gln Gln Met
                725                 730                 735

Ala Pro Ser Thr Gly Pro Pro Gln Gln Gln Pro Val Ala Gln Pro
            740                 745                 750

Pro Pro Thr Gln Gly Pro Pro Ala Gln Gly Asn Glu Thr Gln Leu Ile
        755                 760                 765

Ser Phe Asp
    770

<210> SEQ ID NO 3
<211> LENGTH: 2906
<212> TYPE: DNA
<213> ORGANISM: Homo sapiens
<220> FEATURE:
<221> NAME/KEY: CDS
<222> LOCATION: (76)..(2409)

<400> SEQUENCE: 3
gaagcggaag tcggggccg caccagctcg tagcaggaa gcgcccgcgg cgtcgggttt     60
gggctggagg tcgcc atg ggg cga ggc agc ggc acc ttc gag cgt ctc cta    111
              Met Gly Arg Gly Ser Gly Thr Phe Glu Arg Leu Leu
                1               5                   10 gac aag gcg acc agc cag ctc ctg ttg gag aca gat tgg gag tcc att     159
Asp Lys Ala Thr Ser Gln Leu Leu Leu Glu Thr Asp Trp Glu Ser Ile
        15                  20                  25 ttg cag atc tgc gac ctg atc cgc caa ggg gac aca caa gca aaa tat    207
Leu Gln Ile Cys Asp Leu Ile Arg Gln Gly Asp Thr Gln Ala Lys Tyr
    30                  35                  40

```
gct gtg aat tcc atc aag aag aaa gtc aac gac aag aac cca cac gtc      255
Ala Val Asn Ser Ile Lys Lys Lys Val Asn Asp Lys Asn Pro His Val
45              50                  55                  60 gcc ttg tat gcc ctg gag gtc atg gaa tct gtg gta aag aac tgt ggc      303
Ala Leu Tyr Ala Leu Glu Val Met Glu Ser Val Val Lys Asn Cys Gly
                65                  70                  75 cag aca gtt cat gat gag gtg gcc aac aag cag acc atg gag gag ctg      351
Gln Thr Val His Asp Glu Val Ala Asn Lys Gln Thr Met Glu Glu Leu
            80                  85                  90 aag gac ctg ctg aag aga caa gtg gag gta aac gtc cgt aac aag atc      399
Lys Asp Leu Leu Lys Arg Gln Val Glu Val Asn Val Arg Asn Lys Ile
        95                  100                 105 ctg tac ctg atc cag gcc tgg gcg cat gcc ttc cgg aac gag ccc aag      447
Leu Tyr Leu Ile Gln Ala Trp Ala His Ala Phe Arg Asn Glu Pro Lys
    110                 115                 120 tac aag gtg gtc cag gac acc tac cag atc atg aag gtg gag ggg cac      495
Tyr Lys Val Val Gln Asp Thr Tyr Gln Ile Met Lys Val Glu Gly His
125                 130                 135                 140 gtc ttt cca gaa ttc aaa gag agc gat gcc atg ttt gct gcc gag aga      543
Val Phe Pro Glu Phe Lys Glu Ser Asp Ala Met Phe Ala Ala Glu Arg
                145                 150                 155 gcc cca gac tgg gtg gac gct gag gaa tgc cac cgc tgc agg gtg cag      591
Ala Pro Asp Trp Val Asp Ala Glu Glu Cys His Arg Cys Arg Val Gln
            160                 165                 170 ttc ggg gtg atg acc cgt aag cac cac tgc cgg gcg tgt ggg cag ata      639
Phe Gly Val Met Thr Arg Lys His His Cys Arg Ala Cys Gly Gln Ile
        175                 180                 185 ttc tgt gga aag tgt tct tcc aag tac tcc acc atc ccc aag ttt ggc      687
Phe Cys Gly Lys Cys Ser Ser Lys Tyr Ser Thr Ile Pro Lys Phe Gly
    190                 195                 200 atc gag aag gag gtg cgc gtg tgt gag ccc tgc tac gag cag ctg aac      735
Ile Glu Lys Glu Val Arg Val Cys Glu Pro Cys Tyr Glu Gln Leu Asn
205                 210                 215                 220 agg aaa gcg gag gga aag gcc act tcc acc act gag ctg ccc ccc gag      783
Arg Lys Ala Glu Gly Lys Ala Thr Ser Thr Thr Glu Leu Pro Pro Glu
                225                 230                 235 tac ctg acc agc ccc ctg tct cag cag tcc cag ctg ccc ccc aag agg      831
Tyr Leu Thr Ser Pro Leu Ser Gln Gln Ser Gln Leu Pro Pro Lys Arg
            240                 245                 250 gac gag acg gcc ctg cag gag gag gag gag ctg cag ctg gcc ctg gcg      879
Asp Glu Thr Ala Leu Gln Glu Glu Glu Glu Leu Gln Leu Ala Leu Ala
        255                 260                 265 ctg tca cag tca gag gcg gag gag aag gag agg ctg aga cag aag tcc      927
Leu Ser Gln Ser Glu Ala Glu Glu Lys Glu Arg Leu Arg Gln Lys Ser
    270                 275                 280 acg tac act tcg tac ccc aag gcg gag ccc atg ccc tcg gcc tcc tca      975
Thr Tyr Thr Ser Tyr Pro Lys Ala Glu Pro Met Pro Ser Ala Ser Ser
285                 290                 295                 300 gcg ccc ccc gcc agc agc ctg tac tct tca cct gtg aac tcg tcg gcg     1023
Ala Pro Pro Ala Ser Ser Leu Tyr Ser Ser Pro Val Asn Ser Ser Ala
                305                 310                 315 cct ctg gct gag gac atc gac cct gag ctc gca cgg tat ctc aac cgg     1071
Pro Leu Ala Glu Asp Ile Asp Pro Glu Leu Ala Arg Tyr Leu Asn Arg
            320                 325                 330 aac tac tgg gag aag aag cag gag gag gct cgc aag agc ccc acg cca     1119
Asn Tyr Trp Glu Lys Lys Gln Glu Glu Ala Arg Lys Ser Pro Thr Pro
        335                 340                 345 tct gcg ccc gtg ccc ctg acg gag ccg gct gca cag cct ggg gaa ggg     1167
Ser Ala Pro Val Pro Leu Thr Glu Pro Ala Ala Gln Pro Gly Glu Gly
    350                 355                 360
```

```
cac gca gcc ccc acc aac gtg gtg gag aac ccc ctc ccg gag aca gac    1215
His Ala Ala Pro Thr Asn Val Val Glu Asn Pro Leu Pro Glu Thr Asp
365                 370                 375                 380 tct cag ccc att cct ccc tct ggt ggc ccc ttt agt gag cca cag ttc    1263
Ser Gln Pro Ile Pro Pro Ser Gly Gly Pro Phe Ser Glu Pro Gln Phe
                385                 390                 395 cac aat ggc gag tct gag gag agc cac gag cag ttc ctg aag gcg ctg    1311
His Asn Gly Glu Ser Glu Glu Ser His Glu Gln Phe Leu Lys Ala Leu
            400                 405                 410 cag aac gcc gtc acc acc ttc gtg aac cgc atg aag agt aac cac atg    1359
Gln Asn Ala Val Thr Thr Phe Val Asn Arg Met Lys Ser Asn His Met
        415                 420                 425 cgg ggc cgc agc atc acc aat gac tcg gcc gtg ctc tca ctc ttc cag    1407
Arg Gly Arg Ser Ile Thr Asn Asp Ser Ala Val Leu Ser Leu Phe Gln
    430                 435                 440 tcc atc aac ggc atg cac ccg cag ctg ctg gag ctg ctc aac cag ctg    1455
Ser Ile Asn Gly Met His Pro Gln Leu Leu Glu Leu Leu Asn Gln Leu
445                 450                 455                 460 gac gag cgc agg ctg tac tat gag ggg ctg cag gac aag ctg gca cag    1503
Asp Glu Arg Arg Leu Tyr Tyr Glu Gly Leu Gln Asp Lys Leu Ala Gln
                465                 470                 475 atc cgc gat gcc cgg ggg gcg ctg agt gcc ctg cgc gaa gag cac cgg    1551
Ile Arg Asp Ala Arg Gly Ala Leu Ser Ala Leu Arg Glu Glu His Arg
            480                 485                 490 gag aag ctt cgc cgg gca gcc gag gag gca gag cgc cag cgc cag atc    1599
Glu Lys Leu Arg Arg Ala Ala Glu Glu Ala Glu Arg Gln Arg Gln Ile
        495                 500                 505 cag ctg gcc cag aag ctg gag ata atg cgg cag aag aag cag gag tac    1647
Gln Leu Ala Gln Lys Leu Glu Ile Met Arg Gln Lys Lys Gln Glu Tyr
    510                 515                 520 ctg gag gtg cag agg cag ctg gcc atc cag cgc ctg cag gag cag gag    1695
Leu Glu Val Gln Arg Gln Leu Ala Ile Gln Arg Leu Gln Glu Gln Glu
525                 530                 535                 540 aag gag cgg cag atg cgg ctg gag cag cag aag cag acg gtc cag atg    1743
Lys Glu Arg Gln Met Arg Leu Glu Gln Gln Lys Gln Thr Val Gln Met
                545                 550                 555 cgc gcg cag atg ccc gcc ttc ccc ctg ccc tac gcc cag ctc cag gcc    1791
Arg Ala Gln Met Pro Ala Phe Pro Leu Pro Tyr Ala Gln Leu Gln Ala
            560                 565                 570 atg ccc gca gcc gga ggt gtg ctc tac cag ccc tcg gga cca gcc agc    1839
Met Pro Ala Ala Gly Gly Val Leu Tyr Gln Pro Ser Gly Pro Ala Ser
        575                 580                 585 ttc ccc agc acc ttc agc cct gcc ggc tcg gtg gag ggc tcc cca atg    1887
Phe Pro Ser Thr Phe Ser Pro Ala Gly Ser Val Glu Gly Ser Pro Met
    590                 595                 600 cac ggc gtg tac atg agc cag ccg gcc cct gcc gct ggc ccc tac ccc    1935
His Gly Val Tyr Met Ser Gln Pro Ala Pro Ala Ala Gly Pro Tyr Pro
605                 610                 615                 620 agc atg ccc agc act gcg gct gat ccc agc atg gtg agt gcc tac atg    1983
Ser Met Pro Ser Thr Ala Ala Asp Pro Ser Met Val Ser Ala Tyr Met
                625                 630                 635 tac cca gca ggg gcc act ggg gcg cag gcg gcc ccc cag gcc cag gcc    2031
Tyr Pro Ala Gly Ala Thr Gly Ala Gln Ala Ala Pro Gln Ala Gln Ala
            640                 645                 650 gga ccc acc gcc agc ccc gct tac tca tcc tac cag cct act ccc aca    2079
Gly Pro Thr Ala Ser Pro Ala Tyr Ser Ser Tyr Gln Pro Thr Pro Thr
        655                 660                 665 gcg ggc tac cag aac gtg gcc tcc cag gcc cca cag agc ctc ccg gcc    2127
Ala Gly Tyr Gln Asn Val Ala Ser Gln Ala Pro Gln Ser Leu Pro Ala
```

-continued

```
                   670                 675                 680
atc tct cag cct ccg cag tcc agc acc atg ggc tac atg ggg agc cag      2175
Ile Ser Gln Pro Pro Gln Ser Ser Thr Met Gly Tyr Met Gly Ser Gln
685                 690                 695                 700 tca gtc tcc atg ggc tac cag cct tac aac atg cag aat ctc atg acc      2223
Ser Val Ser Met Gly Tyr Gln Pro Tyr Asn Met Gln Asn Leu Met Thr
                705                 710                 715 acc ctc cca agc cag gat gcg tct ctg cca ccc cag cag ccc tac atc      2271
Thr Leu Pro Ser Gln Asp Ala Ser Leu Pro Pro Gln Gln Pro Tyr Ile
            720                 725                 730 gcg ggg cag cag ccc atg tac cag cag atg gca ccc tct ggc ggt ccc      2319
Ala Gly Gln Gln Pro Met Tyr Gln Gln Met Ala Pro Ser Gly Gly Pro
        735                 740                 745 ccc cag cag cag ccc ccc gtg gcc cag caa ccg cag gca cag ggg ccg      2367
Pro Gln Gln Gln Pro Pro Val Ala Gln Gln Pro Gln Ala Gln Gly Pro
    750                 755                 760 ccg gca cag ggc agc gag gcc cag ctc att tca ttc gac tga              2409
Pro Ala Gln Gly Ser Glu Ala Gln Leu Ile Ser Phe Asp
765                 770                 775 cccaggccat gctcacgtcc ggagtaacac tacatacagt tcacctgaaa cgcctcgtct    2469
ctaactgccg tcgtcctgcc tcctgtcct ctactgccgg tagtgtccct tctctgcgag    2529
tgagggggggg ccttcacccc aagcccacct cccttgtcct cagcctactg cagtccctga   2589
gttagtctct gctttctttc cccagggctg ggccatgggg agggaaggac tttctcccag   2649
gggaagcccc cagccctgtg ggtcatggtc tgtgagaggt ggcaggaatg ggaccctca    2709
cccccccaagc agcctgtgcc ctctggccgc actgtgagct ggctgtggtg tctgggtgtg   2769
gcctggggct ccctctgcag gggcctctct cggcagccac agccaagggt ggaggcttca   2829
ggtctccagc ttctctgctt ctcagctgcc atctccagtg ccccagaatg gtacagcgat   2889
aataaaatgt atttcag                                                   2906
```

<210> SEQ ID NO 4
<211> LENGTH: 777
<212> TYPE: PRT
<213> ORGANISM: Homo sapiens

<400> SEQUENCE: 4

```
Met Gly Arg Gly Ser Gly Thr Phe Glu Arg Leu Leu Asp Lys Ala Thr
1               5                   10                  15

Ser Gln Leu Leu Leu Glu Thr Asp Trp Glu Ser Ile Leu Gln Ile Cys
            20                  25                  30

Asp Leu Ile Arg Gln Gly Asp Thr Gln Ala Lys Tyr Ala Val Asn Ser
        35                  40                  45

Ile Lys Lys Lys Val Asn Asp Lys Asn Pro His Val Ala Leu Tyr Ala
    50                  55                  60

Leu Glu Val Met Glu Ser Val Val Lys Asn Cys Gly Gln Thr Val His
65                  70                  75                  80

Asp Glu Val Ala Asn Lys Gln Thr Met Glu Glu Leu Lys Asp Leu Leu
                85                  90                  95

Lys Arg Gln Val Glu Val Asn Val Arg Asn Lys Ile Leu Tyr Leu Ile
            100                 105                 110

Gln Ala Trp Ala His Ala Phe Arg Asn Glu Pro Lys Tyr Lys Val Val
        115                 120                 125

Gln Asp Thr Tyr Gln Ile Met Lys Val Glu Gly His Val Phe Pro Glu
    130                 135                 140
```

```
Phe Lys Glu Ser Asp Ala Met Phe Ala Ala Glu Arg Ala Pro Asp Trp
145                 150                 155                 160

Val Asp Ala Glu Glu Cys His Arg Cys Arg Val Gln Phe Gly Val Met
            165                 170                 175

Thr Arg Lys His His Cys Arg Ala Cys Gly Gln Ile Phe Cys Gly Lys
            180                 185                 190

Cys Ser Ser Lys Tyr Ser Thr Ile Pro Lys Phe Gly Ile Glu Lys Glu
            195                 200                 205

Val Arg Val Cys Glu Pro Cys Tyr Glu Gln Leu Asn Arg Lys Ala Glu
        210                 215                 220

Gly Lys Ala Thr Ser Thr Thr Glu Leu Pro Pro Glu Tyr Leu Thr Ser
225                 230                 235                 240

Pro Leu Ser Gln Gln Ser Gln Leu Pro Pro Lys Arg Asp Glu Thr Ala
            245                 250                 255

Leu Gln Glu Glu Glu Glu Leu Gln Leu Ala Leu Ala Leu Ser Gln Ser
            260                 265                 270

Glu Ala Glu Glu Lys Glu Arg Leu Arg Gln Lys Ser Thr Tyr Thr Ser
        275                 280                 285

Tyr Pro Lys Ala Glu Pro Met Pro Ser Ala Ser Ser Ala Pro Pro Ala
290                 295                 300

Ser Ser Leu Tyr Ser Ser Pro Val Asn Ser Ser Ala Pro Leu Ala Glu
305                 310                 315                 320

Asp Ile Asp Pro Glu Leu Ala Arg Tyr Leu Asn Arg Asn Tyr Trp Glu
            325                 330                 335

Lys Lys Gln Glu Glu Ala Arg Lys Ser Pro Thr Pro Ser Ala Pro Val
            340                 345                 350

Pro Leu Thr Glu Pro Ala Ala Gln Pro Gly Glu Gly His Ala Ala Pro
            355                 360                 365

Thr Asn Val Val Glu Asn Pro Leu Pro Glu Thr Asp Ser Gln Pro Ile
            370                 375                 380

Pro Pro Ser Gly Gly Pro Phe Ser Glu Pro Gln Phe His Asn Gly Glu
385                 390                 395                 400

Ser Glu Glu Ser His Glu Gln Phe Leu Lys Ala Leu Gln Asn Ala Val
            405                 410                 415

Thr Thr Phe Val Asn Arg Met Lys Ser Asn His Met Arg Gly Arg Ser
            420                 425                 430

Ile Thr Asn Asp Ser Ala Val Leu Ser Leu Phe Gln Ser Ile Asn Gly
            435                 440                 445

Met His Pro Gln Leu Leu Glu Leu Leu Asn Gln Leu Asp Glu Arg Arg
450                 455                 460

Leu Tyr Tyr Glu Gly Leu Gln Asp Lys Leu Ala Gln Ile Arg Asp Ala
465                 470                 475                 480

Arg Gly Ala Leu Ser Ala Leu Arg Glu Glu His Arg Glu Lys Leu Arg
            485                 490                 495

Arg Ala Ala Glu Glu Ala Glu Arg Gln Arg Gln Ile Gln Leu Ala Gln
            500                 505                 510

Lys Leu Glu Ile Met Arg Gln Lys Lys Gln Glu Tyr Leu Glu Val Gln
            515                 520                 525

Arg Gln Leu Ala Ile Gln Arg Leu Gln Glu Gln Glu Lys Glu Arg Gln
            530                 535                 540

Met Arg Leu Glu Gln Gln Lys Gln Thr Val Gln Met Arg Ala Gln Met
545                 550                 555                 560

Pro Ala Phe Pro Leu Pro Tyr Ala Gln Leu Gln Ala Met Pro Ala Ala
```

-continued

```
                   565                 570                 575
Gly Gly Val Leu Tyr Gln Pro Ser Gly Pro Ala Ser Phe Pro Ser Thr
            580                 585                 590

Phe Ser Pro Ala Gly Ser Val Glu Gly Ser Pro Met His Gly Val Tyr
        595                 600                 605

Met Ser Gln Pro Ala Pro Ala Ala Gly Pro Tyr Pro Ser Met Pro Ser
    610                 615                 620

Thr Ala Ala Asp Pro Ser Met Val Ser Ala Tyr Met Tyr Pro Ala Gly
625                 630                 635                 640

Ala Thr Gly Ala Gln Ala Ala Pro Gln Ala Gln Ala Gly Pro Thr Ala
                645                 650                 655

Ser Pro Ala Tyr Ser Ser Tyr Gln Pro Thr Pro Thr Ala Gly Tyr Gln
            660                 665                 670

Asn Val Ala Ser Gln Ala Pro Gln Ser Leu Pro Ala Ile Ser Gln Pro
        675                 680                 685

Pro Gln Ser Ser Thr Met Gly Tyr Met Gly Ser Gln Ser Val Ser Met
    690                 695                 700

Gly Tyr Gln Pro Tyr Asn Met Gln Asn Leu Met Thr Thr Leu Pro Ser
705                 710                 715                 720

Gln Asp Ala Ser Leu Pro Pro Gln Pro Tyr Ile Ala Gly Gln Gln
                725                 730                 735

Pro Met Tyr Gln Gln Met Ala Pro Ser Gly Gly Pro Gln Gln Gln
            740                 745                 750

Pro Pro Val Ala Gln Gln Pro Gln Ala Gln Gly Pro Pro Ala Gln Gly
        755                 760                 765

Ser Glu Ala Gln Leu Ile Ser Phe Asp
    770                 775

<210> SEQ ID NO 5
<211> LENGTH: 2458
<212> TYPE: DNA
<213> ORGANISM: Mus musculus
<220> FEATURE:
<221> NAME/KEY: CDS
<222> LOCATION: (43)..(2370)

<400> SEQUENCE: 5
aaagagggag cgactgcagc gtcggtccgg agtggggtcg cc atg ggg cga ggc        54
                                                 Met Gly Arg Gly
                                                   1 agc ggc acc ttc gag cgt ctc cta gac aaa gcc acc agc cag ctt ctg      102
Ser Gly Thr Phe Glu Arg Leu Leu Asp Lys Ala Thr Ser Gln Leu Leu
  5              10                  15                  20 ttg gag aca gac tgg gag tcc att cta cag atc tgc gac ctg atc cgt      150
Leu Glu Thr Asp Trp Glu Ser Ile Leu Gln Ile Cys Asp Leu Ile Arg
                 25                  30                  35 cag ggg gac aca caa gca aaa tat gct gta aac tcc atc aag aag aag      198
Gln Gly Asp Thr Gln Ala Lys Tyr Ala Val Asn Ser Ile Lys Lys Lys
             40                  45                  50 gtt aat gat aag aac cca cac gtg gct ttg tat gct ctg gag gtg atg      246
Val Asn Asp Lys Asn Pro His Val Ala Leu Tyr Ala Leu Glu Val Met
         55                  60                  65 gag tct gtg gta aag aac tgt ggc cag aca gtc cat gat gaa gtg gcc      294
Glu Ser Val Val Lys Asn Cys Gly Gln Thr Val His Asp Glu Val Ala
     70                  75                  80 aac aaa cag acc atg gaa gaa ctg aag gag ctg ctg aag agg caa gtg      342
Asn Lys Gln Thr Met Glu Glu Leu Lys Glu Leu Leu Lys Arg Gln Val
 85                  90                  95                 100
```

| | | |
|---|---|---|
| gaa gtt aat gtt cgg aac aag atc ttg tac ctg atc cag gcc tgg gca<br>Glu Val Asn Val Arg Asn Lys Ile Leu Tyr Leu Ile Gln Ala Trp Ala<br>              105               110               115 | 390 |
| cat gcc ttc cgg aac gaa ccc aag tac aag gtg gtc cag gac aca tac<br>His Ala Phe Arg Asn Glu Pro Lys Tyr Lys Val Val Gln Asp Thr Tyr<br>        120                 125                130 | 438 |
| cag atc atg aag gta gaa gga cat gtc ttc cct gaa ttt aag gaa agt<br>Gln Ile Met Lys Val Glu Gly His Val Phe Pro Glu Phe Lys Glu Ser<br>           135                140              145 | 486 |
| gat gcc atg ttc gct gct gaa aga gcc cct gac tgg gtg gat gct gag<br>Asp Ala Met Phe Ala Ala Glu Arg Ala Pro Asp Trp Val Asp Ala Glu<br>150                 155                160 | 534 |
| gaa tgc cat cgg tgc aga gta cag ttt ggg gtg gtg acc cgc aag cat<br>Glu Cys His Arg Cys Arg Val Gln Phe Gly Val Val Thr Arg Lys His<br>165                 170               175              180 | 582 |
| cac tgc cga gca tgt ggg cag atc ttc tgt ggc aag tgc tcc tcc aag<br>His Cys Arg Ala Cys Gly Gln Ile Phe Cys Gly Lys Cys Ser Ser Lys<br>                185               190              195 | 630 |
| tac tcc acc atc ccc aag ttc ggc att gag aag gag gtg cgc gtg tgt<br>Tyr Ser Thr Ile Pro Lys Phe Gly Ile Glu Lys Glu Val Arg Val Cys<br>              200                205              210 | 678 |
| gag ccc tgc tat gag cag ctg aac aag aag gca gaa ggg aag gct tcc<br>Glu Pro Cys Tyr Glu Gln Leu Asn Lys Lys Ala Glu Gly Lys Ala Ser<br>           215                220               225 | 726 |
| tct acc act gag ctg ccc cca gag tac ctg acc agc ccc ctg tca cag<br>Ser Thr Thr Glu Leu Pro Pro Glu Tyr Leu Thr Ser Pro Leu Ser Gln<br>     230                235                240 | 774 |
| cag tct cag ctg ccc cca aag cgg gat gag aca gcc ctg cag gaa gag<br>Gln Ser Gln Leu Pro Pro Lys Arg Asp Glu Thr Ala Leu Gln Glu Glu<br>245                 250               255              260 | 822 |
| gag gag cta cag ctg gct ctg gcc cta tca cag tca gag gct gag gag<br>Glu Glu Leu Gln Leu Ala Leu Ala Leu Ser Gln Ser Glu Ala Glu Glu<br>                265               270              275 | 870 |
| aaa gag agg atg aga cag aaa aca aca tat aca gca cat cca aag gca<br>Lys Glu Arg Met Arg Gln Lys Thr Thr Tyr Thr Ala His Pro Lys Ala<br>           280                285               290 | 918 |
| gag ccc acg ccc ttg gct tcc tct gcg ccc cca gct ggc agc ctg tat<br>Glu Pro Thr Pro Leu Ala Ser Ser Ala Pro Pro Ala Gly Ser Leu Tyr<br>               295               300              305 | 966 |
| tcc tcg cct gtg aac tca tca gca cct ctg gct gag gac atc gac cct<br>Ser Ser Pro Val Asn Ser Ser Ala Pro Leu Ala Glu Asp Ile Asp Pro<br>        310                 315               320 | 1014 |
| gag ctt gca aga tac ctc aac cgg aac tac tgg gag aag aaa cag gag<br>Glu Leu Ala Arg Tyr Leu Asn Arg Asn Tyr Trp Glu Lys Lys Gln Glu<br>325                 330                335               340 | 1062 |
| gaa gca cgg aag agc ccc aca cca tct gca cct gtg ccc ctg aca gag<br>Glu Ala Arg Lys Ser Pro Thr Pro Ser Ala Pro Val Pro Leu Thr Glu<br>                345               350              355 | 1110 |
| cct gct gcc cag cct gga gaa gga cat aca gcc ccc aac agc atg gca<br>Pro Ala Ala Gln Pro Gly Glu Gly His Thr Ala Pro Asn Ser Met Ala<br>                  360               365              370 | 1158 |
| gag gct cct ctt cca gag aca gac tct cag ccc ata act ccc tgc agc<br>Glu Ala Pro Leu Pro Glu Thr Asp Ser Gln Pro Ile Thr Pro Cys Ser<br>        375               380                385 | 1206 |
| ggc ccc ttt agt gag tac cag aat ggg gag tcg gag gag agc cat gag<br>Gly Pro Phe Ser Glu Tyr Gln Asn Gly Glu Ser Glu Glu Ser His Glu<br>           390                395               400 | 1254 |
| cag ttc ctc aag gcc ctg cag aat gcc gtg agc act ttt gtc aac cgc<br>Gln Phe Leu Lys Ala Leu Gln Asn Ala Val Ser Thr Phe Val Asn Arg | 1302 |

```
                405                 410                 415                 420
       atg aag agc aac cac atg cgg gga cgc agc atc acc aac gac tcg gct        1350
       Met Lys Ser Asn His Met Arg Gly Arg Ser Ile Thr Asn Asp Ser Ala
                       425                 430                 435 gtg ctg tca ctc ttc cag tcc atc aac acc atg cac ccg cag ctg ctc        1398
       Val Leu Ser Leu Phe Gln Ser Ile Asn Thr Met His Pro Gln Leu Leu
                       440                 445                 450 gag ctg ctc aac cag ctg gat gag cgc agg ctg tac tac gag ggc ctt        1446
       Glu Leu Leu Asn Gln Leu Asp Glu Arg Arg Leu Tyr Tyr Glu Gly Leu
                       455                 460                 465 cag gac aag ctg gca cag ata cgt gac gcc cga ggg gct ctg agc gcc        1494
       Gln Asp Lys Leu Ala Gln Ile Arg Asp Ala Arg Gly Ala Leu Ser Ala
                470                 475                 480 ctg cgt gaa gaa cac agg gag aag ctg cgc cgg gca gct gag gag gct        1542
       Leu Arg Glu Glu His Arg Glu Lys Leu Arg Arg Ala Ala Glu Glu Ala
       485                 490                 495                 500 gag cgt caa cgc cag atc cag ctg gca cag aaa ctg gag atc atg aga        1590
       Glu Arg Gln Arg Gln Ile Gln Leu Ala Gln Lys Leu Glu Ile Met Arg
                       505                 510                 515 cag aag aag cag gag tac ctg gag gtg cag aga cag cta gct atc cag        1638
       Gln Lys Lys Gln Glu Tyr Leu Glu Val Gln Arg Gln Leu Ala Ile Gln
                       520                 525                 530 cgc ctg cag gaa cag gag aag gaa cgg cag atg cgt ctg gag caa cag        1686
       Arg Leu Gln Glu Gln Glu Lys Glu Arg Gln Met Arg Leu Glu Gln Gln
                       535                 540                 545 aag cag act gtc cag atg cgc gcc cag atg cct gcc ttt ccc ttg cct        1734
       Lys Gln Thr Val Gln Met Arg Ala Gln Met Pro Ala Phe Pro Leu Pro
                550                 555                 560 tat gcc cag ctc cag gct atg ccc acg gct ggg ggt gta ctc tac cag        1782
       Tyr Ala Gln Leu Gln Ala Met Pro Thr Ala Gly Gly Val Leu Tyr Gln
       565                 570                 575                 580 ccc tca ggc cca acc agc ttc cct gcc acc ttc agc cca gca ggc tca        1830
       Pro Ser Gly Pro Thr Ser Phe Pro Ala Thr Phe Ser Pro Ala Gly Ser
                       585                 590                 595 gta gag ggc tct ccg atg cat ggt gtg tat atg agc cag cca gcc cca        1878
       Val Glu Gly Ser Pro Met His Gly Val Tyr Met Ser Gln Pro Ala Pro
                       600                 605                 610 gcc act ggc ccc tac ccc agc atg cct ggc aca aca gca gat ccc agc        1926
       Ala Thr Gly Pro Tyr Pro Ser Met Pro Gly Thr Thr Ala Asp Pro Ser
                       615                 620                 625 atg gtc agc gcc tac atg tac cca aca ggt gcc cct ggg gca cag gca        1974
       Met Val Ser Ala Tyr Met Tyr Pro Thr Gly Ala Pro Gly Ala Gln Ala
                630                 635                 640 gcc cct cag gcc cag gcc ggg ccc acc acc agt cct gcc tac tcc tcc        2022
       Ala Pro Gln Ala Gln Ala Gly Pro Thr Thr Ser Pro Ala Tyr Ser Ser
       645                 650                 655                 660 tac cag ccc aca cca acc cca ggc tac cag agc gtg gct tct cag gcc        2070
       Tyr Gln Pro Thr Pro Thr Pro Gly Tyr Gln Ser Val Ala Ser Gln Ala
                       665                 670                 675 cca cag agc ctc cca gcc atc tca cag cct cca cag acc agc aac ata        2118
       Pro Gln Ser Leu Pro Ala Ile Ser Gln Pro Pro Gln Thr Ser Asn Ile
                       680                 685                 690 ggc tac atg ggg agc cag cca atg tcc atg ggc tac cag ccg tac aat        2166
       Gly Tyr Met Gly Ser Gln Pro Met Ser Met Gly Tyr Gln Pro Tyr Asn
                       695                 700                 705 atg cag aat ctc atg acc gcc ctt ccc ggg cag gat gcg tct ctg cca        2214
       Met Gln Asn Leu Met Thr Ala Leu Pro Gly Gln Asp Ala Ser Leu Pro
                710                 715                 720 gcc cag cag ccc tac atc cca ggg cag cag ccc ctg tac cag cag atg        2262
```

```
Ala Gln Gln Pro Tyr Ile Pro Gly Gln Gln Pro Leu Tyr Gln Gln Met
725                 730                 735                 740 gcc ccc agc acc ggc cct ccc cag cag caa ccc cct gtg gcc cag cca      2310
Ala Pro Ser Thr Gly Pro Pro Gln Gln Gln Pro Pro Val Ala Gln Pro
                745                 750                 755 gcg cct aca cag gga ccg cca gca cag ggc agt gag gcc cag ctc atc      2358
Ala Pro Thr Gln Gly Pro Pro Ala Gln Gly Ser Glu Ala Gln Leu Ile
        760                 765                 770 tcc ttt gac tga ccttgagtct ggcgctcacc atgcagagta acactacagt          2410
Ser Phe Asp
        775 tcaccagaaa ccacttatat gtctaactag ccattcctcg cggccgct                 2458

<210> SEQ ID NO 6
<211> LENGTH: 775
<212> TYPE: PRT
<213> ORGANISM: Mus musculus

<400> SEQUENCE: 6

Met Gly Arg Gly Ser Gly Thr Phe Glu Arg Leu Leu Asp Lys Ala Thr
1               5                   10                  15

Ser Gln Leu Leu Leu Glu Thr Asp Trp Glu Ser Ile Leu Gln Ile Cys
            20                  25                  30

Asp Leu Ile Arg Gln Gly Asp Thr Gln Ala Lys Tyr Ala Val Asn Ser
        35                  40                  45

Ile Lys Lys Lys Val Asn Asp Lys Asn Pro His Val Ala Leu Tyr Ala
    50                  55                  60

Leu Glu Val Met Glu Ser Val Val Lys Asn Cys Gly Gln Thr Val His
65                  70                  75                  80

Asp Glu Val Ala Asn Lys Gln Thr Met Glu Glu Leu Lys Glu Leu Leu
                85                  90                  95

Lys Arg Gln Val Glu Val Asn Val Arg Asn Lys Ile Leu Tyr Leu Ile
            100                 105                 110

Gln Ala Trp Ala His Ala Phe Arg Asn Glu Pro Lys Tyr Lys Val Val
        115                 120                 125

Gln Asp Thr Tyr Gln Ile Met Lys Val Glu Gly His Val Phe Pro Glu
    130                 135                 140

Phe Lys Glu Ser Asp Ala Met Phe Ala Ala Glu Arg Ala Pro Asp Trp
145                 150                 155                 160

Val Asp Ala Glu Glu Cys His Arg Cys Arg Val Gln Phe Gly Val Val
                165                 170                 175

Thr Arg Lys His His Cys Arg Ala Cys Gly Gln Ile Phe Cys Gly Lys
            180                 185                 190

Cys Ser Ser Lys Tyr Ser Thr Ile Pro Lys Phe Gly Ile Glu Lys Glu
        195                 200                 205

Val Arg Val Cys Glu Pro Cys Tyr Glu Gln Leu Asn Lys Lys Ala Glu
    210                 215                 220

Gly Lys Ala Ser Ser Thr Thr Glu Leu Pro Pro Glu Tyr Leu Thr Ser
225                 230                 235                 240

Pro Leu Ser Gln Gln Ser Gln Leu Pro Pro Lys Arg Asp Glu Thr Ala
                245                 250                 255

Leu Gln Glu Glu Glu Glu Leu Gln Leu Ala Leu Ala Leu Ser Gln Ser
            260                 265                 270

Glu Ala Glu Glu Lys Glu Arg Met Arg Gln Lys Thr Thr Tyr Thr Ala
        275                 280                 285
```

```
His Pro Lys Ala Glu Pro Thr Pro Leu Ala Ser Ser Ala Pro Pro Ala
    290                 295                 300

Gly Ser Leu Tyr Ser Ser Pro Val Asn Ser Ser Ala Pro Leu Ala Glu
305                 310                 315                 320

Asp Ile Asp Pro Glu Leu Ala Arg Tyr Leu Asn Arg Asn Tyr Trp Glu
                325                 330                 335

Lys Lys Gln Glu Glu Ala Arg Lys Ser Pro Thr Pro Ser Ala Pro Val
            340                 345                 350

Pro Leu Thr Glu Pro Ala Ala Gln Pro Gly Glu Gly His Thr Ala Pro
        355                 360                 365

Asn Ser Met Ala Glu Ala Pro Leu Pro Glu Thr Asp Ser Gln Pro Ile
370                 375                 380

Thr Pro Cys Ser Gly Pro Phe Ser Glu Tyr Gln Asn Gly Glu Ser Glu
385                 390                 395                 400

Glu Ser His Glu Gln Phe Leu Lys Ala Leu Gln Asn Ala Val Ser Thr
                405                 410                 415

Phe Val Asn Arg Met Lys Ser Asn His Met Arg Gly Arg Ser Ile Thr
            420                 425                 430

Asn Asp Ser Ala Val Leu Ser Leu Phe Gln Ser Ile Asn Thr Met His
        435                 440                 445

Pro Gln Leu Leu Glu Leu Leu Asn Gln Leu Asp Glu Arg Arg Leu Tyr
    450                 455                 460

Tyr Glu Gly Leu Gln Asp Lys Leu Ala Gln Ile Arg Asp Ala Arg Gly
465                 470                 475                 480

Ala Leu Ser Ala Leu Arg Glu Glu His Arg Glu Lys Leu Arg Arg Ala
                485                 490                 495

Ala Glu Glu Ala Glu Arg Gln Arg Gln Ile Gln Leu Ala Gln Lys Leu
            500                 505                 510

Glu Ile Met Arg Gln Lys Lys Gln Glu Tyr Leu Glu Val Gln Arg Gln
        515                 520                 525

Leu Ala Ile Gln Arg Leu Gln Glu Gln Glu Lys Glu Arg Gln Met Arg
530                 535                 540

Leu Glu Gln Gln Lys Gln Thr Val Gln Met Arg Ala Gln Met Pro Ala
545                 550                 555                 560

Phe Pro Leu Pro Tyr Ala Gln Leu Gln Ala Met Pro Thr Ala Gly Gly
                565                 570                 575

Val Leu Tyr Gln Pro Ser Gly Pro Thr Ser Phe Pro Ala Thr Phe Ser
            580                 585                 590

Pro Ala Gly Ser Val Glu Gly Ser Pro Met His Gly Val Tyr Met Ser
        595                 600                 605

Gln Pro Ala Pro Ala Thr Gly Pro Tyr Pro Ser Met Pro Gly Thr Thr
    610                 615                 620

Ala Asp Pro Ser Met Val Ser Ala Tyr Met Tyr Pro Thr Gly Ala Pro
625                 630                 635                 640

Gly Ala Gln Ala Ala Pro Gln Ala Gln Ala Gly Pro Thr Thr Ser Pro
                645                 650                 655

Ala Tyr Ser Ser Tyr Gln Pro Thr Pro Thr Pro Gly Tyr Gln Ser Val
            660                 665                 670

Ala Ser Gln Ala Pro Gln Ser Leu Pro Ala Ile Ser Gln Pro Pro Gln
        675                 680                 685

Thr Ser Asn Ile Gly Tyr Met Gly Ser Gln Pro Met Ser Met Gly Tyr
    690                 695                 700

Gln Pro Tyr Asn Met Gln Asn Leu Met Thr Ala Leu Pro Gly Gln Asp
```

```
                    705                 710                 715                 720
Ala Ser Leu Pro Ala Gln Gln Pro Tyr Ile Pro Gly Gln Gln Pro Leu
                725                 730                 735

Tyr Gln Gln Met Ala Pro Ser Thr Gly Pro Gln Gln Gln Pro Pro
            740                 745                 750

Val Ala Gln Pro Ala Pro Thr Gln Gly Pro Pro Ala Gln Gly Ser Glu
                755                 760                 765

Ala Gln Leu Ile Ser Phe Asp
        770                 775

<210> SEQ ID NO 7
<211> LENGTH: 522
<212> TYPE: DNA
<213> ORGANISM: Rattus norvegicus
<220> FEATURE:
<221> NAME/KEY: CDS
<222> LOCATION: (1)..(522)

<400> SEQUENCE: 7 ggc ccc ttt agt gag cag tac cag aac gcg gag tcg gag gag agc cac      48
Gly Pro Phe Ser Glu Gln Tyr Gln Asn Ala Glu Ser Glu Glu Ser His
1               5                   10                  15 gag cag ttc ctc aag gcc ctg cag aat gca gtc agc act ttt gtc aac      96
Glu Gln Phe Leu Lys Ala Leu Gln Asn Ala Val Ser Thr Phe Val Asn
            20                  25                  30 cgc atg aag agc aac cac atg agg ggc cgc agt atc acc aat gac tcg     144
Arg Met Lys Ser Asn His Met Arg Gly Arg Ser Ile Thr Asn Asp Ser
        35                  40                  45 gct gtg ctg tcc ctc ttc cag tcc atc aat agc aca cac cca cag ctg     192
Ala Val Leu Ser Leu Phe Gln Ser Ile Asn Ser Thr His Pro Gln Leu
    50                  55                  60 ctc gag ctg ctc aac cgg ctg gat gag cgc agg ctg tac tac gag ggg     240
Leu Glu Leu Leu Asn Arg Leu Asp Glu Arg Arg Leu Tyr Tyr Glu Gly
65                  70                  75                  80 ctt cag gac aag ctg gca cag ata cgt gat gcc cga ggg gcc ctg agt     288
Leu Gln Asp Lys Leu Ala Gln Ile Arg Asp Ala Arg Gly Ala Leu Ser
                85                  90                  95 gcc ctg cgt gaa gag cac agg gag aag ctg cgc cgg gca gct gag gag     336
Ala Leu Arg Glu Glu His Arg Glu Lys Leu Arg Arg Ala Ala Glu Glu
            100                 105                 110 gcg gag cgt caa cgt cag atc cag ctg gca cag aag ctg gag atc atg     384
Ala Glu Arg Gln Arg Gln Ile Gln Leu Ala Gln Lys Leu Glu Ile Met
        115                 120                 125 aga caa aag aag cag gag tat ctg gag gtg cag aga cag cta gct atc     432
Arg Gln Lys Lys Gln Glu Tyr Leu Glu Val Gln Arg Gln Leu Ala Ile
    130                 135                 140 cag cgt ctg cag gaa cag gag aag gaa cgg cag atg cgc ctg gag caa     480
Gln Arg Leu Gln Glu Gln Glu Lys Glu Arg Gln Met Arg Leu Glu Gln
145                 150                 155                 160 cag aag cag act gtc cag atg cgt gcc cag atg cct gtc ttc                 522
Gln Lys Gln Thr Val Gln Met Arg Ala Gln Met Pro Val Phe
                165                 170

<210> SEQ ID NO 8
<211> LENGTH: 174
<212> TYPE: PRT
<213> ORGANISM: Rattus norvegicus

<400> SEQUENCE: 8

Gly Pro Phe Ser Glu Gln Tyr Gln Asn Ala Glu Ser Glu Glu Ser His
1               5                   10                  15
```

```
Glu Gln Phe Leu Lys Ala Leu Gln Asn Ala Val Ser Thr Phe Val Asn
             20                  25                  30

Arg Met Lys Ser Asn His Met Arg Gly Arg Ser Ile Thr Asn Asp Ser
         35                  40                  45

Ala Val Leu Ser Leu Phe Gln Ser Ile Asn Ser Thr His Pro Gln Leu
     50                  55                  60

Leu Glu Leu Leu Asn Arg Leu Asp Glu Arg Arg Leu Tyr Tyr Glu Gly
 65                  70                  75                  80

Leu Gln Asp Lys Leu Ala Gln Ile Arg Asp Ala Arg Gly Ala Leu Ser
                 85                  90                  95

Ala Leu Arg Glu Glu His Arg Glu Lys Leu Arg Arg Ala Ala Glu Glu
            100                 105                 110

Ala Glu Arg Gln Arg Gln Ile Gln Leu Ala Gln Lys Leu Glu Ile Met
        115                 120                 125

Arg Gln Lys Lys Gln Glu Tyr Leu Glu Val Gln Arg Gln Leu Ala Ile
    130                 135                 140

Gln Arg Leu Gln Glu Gln Glu Lys Glu Arg Gln Met Arg Leu Glu Gln
145                 150                 155                 160

Gln Lys Gln Thr Val Gln Met Arg Ala Gln Met Pro Val Phe
                165                 170
```

```
<210> SEQ ID NO 9
<211> LENGTH: 519
<212> TYPE: DNA
<213> ORGANISM: Homo sapiens
<220> FEATURE:
<221> NAME/KEY: CDS
<222> LOCATION: (1)..(519)

<400> SEQUENCE: 9 ttt agt gag cca cag ttc cac aat ggc gag tct gag gag agc cac gag      48
Phe Ser Glu Pro Gln Phe His Asn Gly Glu Ser Glu Glu Ser His Glu
1               5                  10                  15 cag ttc ctg aag gcg ctg cag aac gcc gtc acc acc ttc gtg aac cgc      96
Gln Phe Leu Lys Ala Leu Gln Asn Ala Val Thr Thr Phe Val Asn Arg
             20                  25                  30 atg aag agt aac cac atg cgg ggc cgc agc atc acc aat gac tcg gcc     144
Met Lys Ser Asn His Met Arg Gly Arg Ser Ile Thr Asn Asp Ser Ala
         35                  40                  45 gtg ctc tca ctc ttc cag tcc atc aac ggc atg cac ccg cag ctg ctg     192
Val Leu Ser Leu Phe Gln Ser Ile Asn Gly Met His Pro Gln Leu Leu
     50                  55                  60 gag ctg ctc aac cag ctg gac gag cgc agg ctg tac tat gag ggg ctg     240
Glu Leu Leu Asn Gln Leu Asp Glu Arg Arg Leu Tyr Tyr Glu Gly Leu
 65                  70                  75                  80 cag gac aag ctg gca cag atc cgc gat gcc cgg ggg gcg ctg agt gcc     288
Gln Asp Lys Leu Ala Gln Ile Arg Asp Ala Arg Gly Ala Leu Ser Ala
                 85                  90                  95 ctg cgc gaa gag cac cgg gag aag ctt cgc cgg gca gcc gag gag gca     336
Leu Arg Glu Glu His Arg Glu Lys Leu Arg Arg Ala Ala Glu Glu Ala
            100                 105                 110 gag cgc cag cgc cag atc cag ctg gcc cag aag ctg gag ata atg cgg     384
Glu Arg Gln Arg Gln Ile Gln Leu Ala Gln Lys Leu Glu Ile Met Arg
        115                 120                 125 cag aag aag cag gag tac ctg gag gtg cag agg cag ctg gcc atc cag     432
Gln Lys Lys Gln Glu Tyr Leu Glu Val Gln Arg Gln Leu Ala Ile Gln
    130                 135                 140 cgc ctg cag gag cag gag aag gag cgg cag atg cgg ctg gag cag cag     480
Arg Leu Gln Glu Gln Glu Lys Glu Arg Gln Met Arg Leu Glu Gln Gln
```

```
Arg Leu Gln Glu Gln Glu Lys Glu Arg Gln Met Arg Leu Glu Gln Gln
145                 150                 155                 160 aag cag acg gtc cag atg cgc gcg cag atg ccc gcc ttc                        519
Lys Gln Thr Val Gln Met Arg Ala Gln Met Pro Ala Phe
                165                 170

<210> SEQ ID NO 10
<211> LENGTH: 173
<212> TYPE: PRT
<213> ORGANISM: Homo sapiens

<400> SEQUENCE: 10

Phe Ser Glu Pro Gln Phe His Asn Gly Glu Ser Glu Glu Ser His Glu
1               5                   10                  15

Gln Phe Leu Lys Ala Leu Gln Asn Ala Val Thr Thr Phe Val Asn Arg
            20                  25                  30

Met Lys Ser Asn His Met Arg Gly Arg Ser Ile Thr Asn Asp Ser Ala
        35                  40                  45

Val Leu Ser Leu Phe Gln Ser Ile Asn Gly Met His Pro Gln Leu Leu
    50                  55                  60

Glu Leu Leu Asn Gln Leu Asp Glu Arg Arg Leu Tyr Tyr Glu Gly Leu
65                  70                  75                  80

Gln Asp Lys Leu Ala Gln Ile Arg Asp Ala Arg Gly Ala Leu Ser Ala
                85                  90                  95

Leu Arg Glu Glu His Arg Glu Lys Leu Arg Arg Ala Ala Glu Glu Ala
            100                 105                 110

Glu Arg Gln Arg Gln Ile Gln Leu Ala Gln Lys Leu Glu Ile Met Arg
        115                 120                 125

Gln Lys Lys Gln Glu Tyr Leu Glu Val Gln Arg Gln Leu Ala Ile Gln
    130                 135                 140

Arg Leu Gln Glu Gln Glu Lys Glu Arg Gln Met Arg Leu Glu Gln Gln
145                 150                 155                 160

Lys Gln Thr Val Gln Met Arg Ala Gln Met Pro Ala Phe
                165                 170

<210> SEQ ID NO 11
<211> LENGTH: 513
<212> TYPE: DNA
<213> ORGANISM: Mus musculus
<220> FEATURE:
<221> NAME/KEY: CDS
<222> LOCATION: (1)..(513)

<400> SEQUENCE: 11 ggc ccc ttt agt gag tac cag aat ggg gag tcg gag gag agc cat gag         48
Gly Pro Phe Ser Glu Tyr Gln Asn Gly Glu Ser Glu Glu Ser His Glu
1               5                   10                  15 cag ttc ctc aag gcc ctg cag aat gcc gtg agc act ttt gtc aac cgc         96
Gln Phe Leu Lys Ala Leu Gln Asn Ala Val Ser Thr Phe Val Asn Arg
            20                  25                  30 atg aag agc aac cac atg cgg gga cgc agc atc acc aac gac tcg gct        144
Met Lys Ser Asn His Met Arg Gly Arg Ser Ile Thr Asn Asp Ser Ala
        35                  40                  45 gtg ctg tca ctc ttc cag tcc atc aac acc atg cac ccg cag ctg ctc        192
Val Leu Ser Leu Phe Gln Ser Ile Asn Thr Met His Pro Gln Leu Leu
    50                  55                  60 gag ctg ctc aac cag ctg gat gag cgc agg ctg tac tac gag ggc ctt        240
Glu Leu Leu Asn Gln Leu Asp Glu Arg Arg Leu Tyr Tyr Glu Gly Leu
65                  70                  75                  80
```

```
cag gac aag ctg gca cag ata cgt gac gcc cga ggg gct ctg agc gcc      288
Gln Asp Lys Leu Ala Gln Ile Arg Asp Ala Arg Gly Ala Leu Ser Ala
                85                  90                  95 ctg cgt gaa gaa cac agg gag aag ctg cgc cgg gca gct gag gag gct      336
Leu Arg Glu Glu His Arg Glu Lys Leu Arg Arg Ala Ala Glu Glu Ala
            100                 105                 110 gag cgt caa cgc cag atc cag ctg gca cag aaa ctg gag atc atg aga      384
Glu Arg Gln Arg Gln Ile Gln Leu Ala Gln Lys Leu Glu Ile Met Arg
        115                 120                 125 cag aag aag cag gag tac ctg gag gtg cag aga cag cta gct atc cag      432
Gln Lys Lys Gln Glu Tyr Leu Glu Val Gln Arg Gln Leu Ala Ile Gln
    130                 135                 140 cgc ctg cag gaa cag gag aag gaa cgg cag atg cgt ctg gag caa cag      480
Arg Leu Gln Glu Gln Glu Lys Glu Arg Gln Met Arg Leu Glu Gln Gln
145                 150                 155                 160 aag cag act gtc cag atg cgc gcc cag atg cct                          513
Lys Gln Thr Val Gln Met Arg Ala Gln Met Pro
                165                 170
```

```
<210> SEQ ID NO 12
<211> LENGTH: 171
<212> TYPE: PRT
<213> ORGANISM: Mus musculus

<400> SEQUENCE: 12

Gly Pro Phe Ser Glu Tyr Gln Asn Gly Glu Ser Glu Glu Ser His Glu
1               5                   10                  15

Gln Phe Leu Lys Ala Leu Gln Asn Ala Val Ser Thr Phe Val Asn Arg
            20                  25                  30

Met Lys Ser Asn His Met Arg Gly Arg Ser Ile Thr Asn Asp Ser Ala
        35                  40                  45

Val Leu Ser Leu Phe Gln Ser Ile Asn Thr Met His Pro Gln Leu Leu
    50                  55                  60

Glu Leu Leu Asn Gln Leu Asp Glu Arg Arg Leu Tyr Tyr Glu Gly Leu
65                  70                  75                  80

Gln Asp Lys Leu Ala Gln Ile Arg Asp Ala Arg Gly Ala Leu Ser Ala
                85                  90                  95

Leu Arg Glu Glu His Arg Glu Lys Leu Arg Arg Ala Ala Glu Glu Ala
            100                 105                 110

Glu Arg Gln Arg Gln Ile Gln Leu Ala Gln Lys Leu Glu Ile Met Arg
        115                 120                 125

Gln Lys Lys Gln Glu Tyr Leu Glu Val Gln Arg Gln Leu Ala Ile Gln
    130                 135                 140

Arg Leu Gln Glu Gln Glu Lys Glu Arg Gln Met Arg Leu Glu Gln Gln
145                 150                 155                 160

Lys Gln Thr Val Gln Met Arg Ala Gln Met Pro
                165                 170
```

```
<210> SEQ ID NO 13
<211> LENGTH: 20
<212> TYPE: PRT
<213> ORGANISM: Artificial
<220> FEATURE:
<223> OTHER INFORMATION: Synthetic peptide

<400> SEQUENCE: 13

Met Lys Ser Asn His Met Arg Gly Arg Ser Ile Thr Asn Asp Ser Ala
1               5                   10                  15

Val Leu Ser Leu
```

```
                 20

<210> SEQ ID NO 14
<211> LENGTH: 20
<212> TYPE: PRT
<213> ORGANISM: Artificial
<220> FEATURE:
<223> OTHER INFORMATION: Synthetic peptide

<400> SEQUENCE: 14

Ile Thr Asn Asp Ser Ala Val Leu Ser Leu Phe Gln Ser Ile Asn Thr
1               5                   10                  15

Met His Pro Gln
                 20

<210> SEQ ID NO 15
<211> LENGTH: 20
<212> TYPE: PRT
<213> ORGANISM: Artificial
<220> FEATURE:
<223> OTHER INFORMATION: Synthetic peptide

<400> SEQUENCE: 15

Phe Gln Ser Ile Asn Thr Met His Pro Gln Leu Leu Glu Leu Leu Asn
1               5                   10                  15

Gln Leu Asp Glu
                 20

<210> SEQ ID NO 16
<211> LENGTH: 20
<212> TYPE: PRT
<213> ORGANISM: Artificial
<220> FEATURE:
<223> OTHER INFORMATION: Synthetic peptide

<400> SEQUENCE: 16

Leu Leu Glu Leu Leu Asn Gln Leu Asp Glu Arg Arg Leu Tyr Tyr Glu
1               5                   10                  15

Gly Leu Gln Asp
                 20

<210> SEQ ID NO 17
<211> LENGTH: 20
<212> TYPE: PRT
<213> ORGANISM: Artificial
<220> FEATURE:
<223> OTHER INFORMATION: Synthetic peptide

<400> SEQUENCE: 17

Arg Arg Leu Tyr Tyr Glu Gly Leu Gln Asp Lys Leu Ala Gln Ile Arg
1               5                   10                  15

Asp Ala Arg Gly
                 20

<210> SEQ ID NO 18
<211> LENGTH: 20
<212> TYPE: PRT
<213> ORGANISM: Artificial
<220> FEATURE:
<223> OTHER INFORMATION: Synthetic peptide

<400> SEQUENCE: 18

Lys Leu Ala Gln Ile Arg Asp Ala Arg Gly Ala Leu Ser Ala Leu Arg
1               5                   10                  15
```

```
Glu Glu His Arg
            20

<210> SEQ ID NO 19
<211> LENGTH: 20
<212> TYPE: PRT
<213> ORGANISM: Artificial
<220> FEATURE:
<223> OTHER INFORMATION: Synthetic peptide

<400> SEQUENCE: 19

Ala Leu Ser Ala Leu Arg Glu Glu His Arg Glu Lys Leu Arg Arg Ala
1               5                   10                  15

Ala Glu Glu Ala
            20

<210> SEQ ID NO 20
<211> LENGTH: 20
<212> TYPE: PRT
<213> ORGANISM: Artificial
<220> FEATURE:
<223> OTHER INFORMATION: Synthetic peptide

<400> SEQUENCE: 20

Glu Lys Leu Arg Arg Ala Ala Glu Glu Ala Glu Arg Gln Arg Gln Ile
1               5                   10                  15

Gln Leu Ala Gln
            20

<210> SEQ ID NO 21
<211> LENGTH: 20
<212> TYPE: PRT
<213> ORGANISM: Artificial
<220> FEATURE:
<223> OTHER INFORMATION: Synthetic peptide

<400> SEQUENCE: 21

Glu Arg Gln Arg Gln Ile Gln Leu Ala Gln Lys Leu Glu Ile Met Arg
1               5                   10                  15

Gln Lys Lys Gln
            20

<210> SEQ ID NO 22
<211> LENGTH: 20
<212> TYPE: PRT
<213> ORGANISM: Artificial
<220> FEATURE:
<223> OTHER INFORMATION: Synthetic peptide

<400> SEQUENCE: 22

Lys Leu Glu Ile Met Arg Gln Lys Lys Gln Glu Tyr Leu Glu Val Gln
1               5                   10                  15

Arg Gln Leu Ala
            20

<210> SEQ ID NO 23
<211> LENGTH: 20
<212> TYPE: PRT
<213> ORGANISM: Artificial
<220> FEATURE:
<223> OTHER INFORMATION: Synthetic peptide

<400> SEQUENCE: 23

Glu Tyr Leu Glu Val Gln Arg Gln Leu Ala Ile Gln Arg Leu Gln Glu
1               5                   10                  15
```

Gln Glu Lys Glu
            20

<210> SEQ ID NO 24
<211> LENGTH: 20
<212> TYPE: PRT
<213> ORGANISM: Artificial
<220> FEATURE:
<223> OTHER INFORMATION: Synthetic peptide

<400> SEQUENCE: 24

Ile Gln Arg Leu Gln Glu Gln Glu Lys Glu Arg Gln Met Arg Leu Glu
1               5                   10                  15

Gln Gln Lys Gln
            20

<210> SEQ ID NO 25
<211> LENGTH: 20
<212> TYPE: PRT
<213> ORGANISM: Artificial
<220> FEATURE:
<223> OTHER INFORMATION: Synthetic peptide

<400> SEQUENCE: 25

Arg Gln Met Arg Leu Glu Gln Gln Lys Gln Thr Val Gln Met Arg Ala
1               5                   10                  15

Gln Met Pro Ala
            20

<210> SEQ ID NO 26
<211> LENGTH: 10
<212> TYPE: PRT
<213> ORGANISM: Artificial
<220> FEATURE:
<223> OTHER INFORMATION: Synthetic peptide

<400> SEQUENCE: 26

Met Gly Arg Gly Ser Gly Thr Phe Glu Arg
1               5                   10

<210> SEQ ID NO 27
<211> LENGTH: 10
<212> TYPE: PRT
<213> ORGANISM: Artificial
<220> FEATURE:
<223> OTHER INFORMATION: Synthetic peptide

<400> SEQUENCE: 27

Phe Gln Ser Ile Asn Thr Met His Pro Gln
1               5                   10

<210> SEQ ID NO 28
<211> LENGTH: 10
<212> TYPE: PRT
<213> ORGANISM: Artificial
<220> FEATURE:
<223> OTHER INFORMATION: Synthetic peptide

<400> SEQUENCE: 28

Lys Leu Ala Gln Ile Arg Asp Ala Arg Gly
1               5                   10

<210> SEQ ID NO 29
<211> LENGTH: 10
<212> TYPE: PRT

```
<213> ORGANISM: Artificial
<220> FEATURE:
<223> OTHER INFORMATION: Synthetic peptide

<400> SEQUENCE: 29

Ala Leu Ser Ala Leu Arg Glu Glu His Arg
1               5                   10

<210> SEQ ID NO 30
<211> LENGTH: 10
<212> TYPE: PRT
<213> ORGANISM: Artificial
<220> FEATURE:
<223> OTHER INFORMATION: Synthetic peptide

<400> SEQUENCE: 30

Glu Lys Leu Arg Arg Ala Ala Glu Glu Ala
1               5                   10

<210> SEQ ID NO 31
<211> LENGTH: 10
<212> TYPE: PRT
<213> ORGANISM: Artificial
<220> FEATURE:
<223> OTHER INFORMATION: Synthetic peptide

<400> SEQUENCE: 31

Glu Arg Gln Arg Gln Ile Gln Leu Ala Gln
1               5                   10

<210> SEQ ID NO 32
<211> LENGTH: 10
<212> TYPE: PRT
<213> ORGANISM: Artificial
<220> FEATURE:
<223> OTHER INFORMATION: Synthetic peptide

<400> SEQUENCE: 32

Lys Leu Glu Ile Met Arg Gln Lys Lys Gln
1               5                   10

<210> SEQ ID NO 33
<211> LENGTH: 10
<212> TYPE: PRT
<213> ORGANISM: Artificial
<220> FEATURE:
<223> OTHER INFORMATION: Synthetic peptide

<400> SEQUENCE: 33

Glu Tyr Leu Glu Val Gln Arg Gln Leu Ala
1               5                   10

<210> SEQ ID NO 34
<211> LENGTH: 10
<212> TYPE: PRT
<213> ORGANISM: Artificial
<220> FEATURE:
<223> OTHER INFORMATION: Synthetic peptide

<400> SEQUENCE: 34

Ile Gln Arg Leu Gln Glu Gln Glu Lys Glu
1               5                   10

<210> SEQ ID NO 35
<211> LENGTH: 10
<212> TYPE: PRT
<213> ORGANISM: Artificial
```

```
<220> FEATURE:
<223> OTHER INFORMATION: Synthetic peptide

<400> SEQUENCE: 35

Leu Asp Glu Arg Arg Leu Tyr Tyr Glu Gly
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic peptide

<400> SEQUENCE: 36

Asp Glu Arg Arg Leu Tyr Tyr Glu Gly Leu
1               5                   10

<210> SEQ ID NO 37
<211> LENGTH: 10
<212> TYPE: PRT
<213> ORGANISM: Artificial
<220> FEATURE:
<223> OTHER INFORMATION: Synthetic peptide

<400> SEQUENCE: 37

Glu Arg Arg Leu Tyr Tyr Glu Gly Leu Gln
1               5                   10

<210> SEQ ID NO 38
<211> LENGTH: 10
<212> TYPE: PRT
<213> ORGANISM: Artificial
<220> FEATURE:
<223> OTHER INFORMATION: Synthetic peptide

<400> SEQUENCE: 38

Arg Arg Leu Tyr Tyr Glu Gly Leu Gln Asp
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic peptide

<400> SEQUENCE: 39

Arg Leu Tyr Tyr Glu Gly Leu Gln Asp Lys
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic peptide

<400> SEQUENCE: 40

Leu Tyr Tyr Glu Gly Leu Gln Asp Lys Leu
1               5                   10

<210> SEQ ID NO 41
<211> LENGTH: 10
<212> TYPE: PRT
<213> ORGANISM: Artificial
<220> FEATURE:
```

<223> OTHER INFORMATION: Synthetic peptide

<400> SEQUENCE: 41

Tyr Tyr Glu Gly Leu Gln Asp Lys Leu Ala
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic peptide

<400> SEQUENCE: 42

Tyr Glu Gly Leu Gln Asp Lys Leu Ala Gln
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic peptide

<400> SEQUENCE: 43

Glu Gly Leu Gln Asp Lys Leu Ala Gln Ile
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic peptide

<400> SEQUENCE: 44

Gly Leu Gln Asp Lys Leu Ala Gln Ile Arg
1               5                   10

<210> SEQ ID NO 45
<211> LENGTH: 10
<212> TYPE: PRT
<213> ORGANISM: Artificial
<220> FEATURE:
<223> OTHER INFORMATION: Synthetic peptide

<400> SEQUENCE: 45

Leu Gln Asp Lys Leu Ala Gln Ile Arg Asp
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic peptide

<400> SEQUENCE: 46

Glu Arg Gln Arg Gln Ile Gln Leu Ala Gln
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic peptide

```
<400> SEQUENCE: 47

Arg Gln Arg Gln Ile Gln Leu Ala Gln Lys
1               5                   10

<210> SEQ ID NO 48
<211> LENGTH: 10
<212> TYPE: PRT
<213> ORGANISM: Artificial
<220> FEATURE:
<223> OTHER INFORMATION: Synthetic peptide

<400> SEQUENCE: 48

Gln Arg Gln Ile Gln Leu Ala Gln Lys Leu
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic peptide

<400> SEQUENCE: 49

Arg Gln Ile Gln Leu Ala Gln Lys Leu Glu
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic peptide

<400> SEQUENCE: 50

Gln Ile Gln Leu Ala Gln Lys Leu Glu Ile
1               5                   10

<210> SEQ ID NO 51
<211> LENGTH: 10
<212> TYPE: PRT
<213> ORGANISM: Artificial
<220> FEATURE:
<223> OTHER INFORMATION: Synthetic peptide

<400> SEQUENCE: 51

Ile Gln Leu Ala Gln Lys Leu Glu Ile Met
1               5                   10

<210> SEQ ID NO 52
<211> LENGTH: 10
<212> TYPE: PRT
<213> ORGANISM: Artificial
<220> FEATURE:
<223> OTHER INFORMATION: Synthetic peptide

<400> SEQUENCE: 52

Gln Leu Ala Gln Lys Leu Glu Ile Met Arg
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic peptide
```

```
<400> SEQUENCE: 53

Leu Ala Gln Lys Leu Glu Ile Met Arg Gln
1               5                   10

<210> SEQ ID NO 54
<211> LENGTH: 10
<212> TYPE: PRT
<213> ORGANISM: Artificial
<220> FEATURE:
<223> OTHER INFORMATION: Synthetic peptide

<400> SEQUENCE: 54

Ala Gln Lys Leu Glu Ile Met Arg Gln Lys
1               5                   10

<210> SEQ ID NO 55
<211> LENGTH: 10
<212> TYPE: PRT
<213> ORGANISM: Artificial
<220> FEATURE:
<223> OTHER INFORMATION: Synthetic peptide

<400> SEQUENCE: 55

Glu Tyr Leu Glu Val Gln Arg Gln Leu Ala
1               5                   10

<210> SEQ ID NO 56
<211> LENGTH: 10
<212> TYPE: PRT
<213> ORGANISM: Artificial
<220> FEATURE:
<223> OTHER INFORMATION: Synthetic peptide

<400> SEQUENCE: 56

Tyr Leu Glu Val Gln Arg Gln Leu Ala Ile
1               5                   10

<210> SEQ ID NO 57
<211> LENGTH: 10
<212> TYPE: PRT
<213> ORGANISM: Artificial
<220> FEATURE:
<223> OTHER INFORMATION: Synthetic peptide

<400> SEQUENCE: 57

Leu Glu Val Gln Arg Gln Leu Ala Ile Gln
1               5                   10

<210> SEQ ID NO 58
<211> LENGTH: 10
<212> TYPE: PRT
<213> ORGANISM: Artificial
<220> FEATURE:
<223> OTHER INFORMATION: Synthetic peptide

<400> SEQUENCE: 58

Glu Val Gln Arg Gln Leu Ala Ile Gln Arg
1               5                   10

<210> SEQ ID NO 59
<211> LENGTH: 10
<212> TYPE: PRT
<213> ORGANISM: Artificial
<220> FEATURE:
<223> OTHER INFORMATION: Synthetic peptide

<400> SEQUENCE: 59
```

Val Gln Arg Gln Leu Ala Ile Gln Arg Leu
1               5                   10

<210> SEQ ID NO 60
<211> LENGTH: 10
<212> TYPE: PRT
<213> ORGANISM: Artificial
<220> FEATURE:
<223> OTHER INFORMATION: Synthetic peptide

<400> SEQUENCE: 60

Gln Arg Gln Leu Ala Ile Gln Arg Leu Gln
1               5                   10

<210> SEQ ID NO 61
<211> LENGTH: 10
<212> TYPE: PRT
<213> ORGANISM: Artificial
<220> FEATURE:
<223> OTHER INFORMATION: Synthetic peptide

<400> SEQUENCE: 61

Arg Gln Leu Ala Ile Gln Arg Leu Gln Glu
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic peptide

<400> SEQUENCE: 62

Gln Leu Ala Ile Gln Arg Leu Gln Glu Gln
1               5                   10

<210> SEQ ID NO 63
<211> LENGTH: 10
<212> TYPE: PRT
<213> ORGANISM: Artificial
<220> FEATURE:
<223> OTHER INFORMATION: Synthetic peptide

<400> SEQUENCE: 63

Leu Ala Ile Gln Arg Leu Gln Glu Gln Glu
1               5                   10

<210> SEQ ID NO 64
<211> LENGTH: 10
<212> TYPE: PRT
<213> ORGANISM: Artificial
<220> FEATURE:
<223> OTHER INFORMATION: Synthetic peptide

<400> SEQUENCE: 64

Ala Ile Gln Arg Leu Gln Glu Gln Glu Lys
1               5                   10

<210> SEQ ID NO 65
<211> LENGTH: 12
<212> TYPE: PRT
<213> ORGANISM: Artificial
<220> FEATURE:
<223> OTHER INFORMATION: Synthetic peptide

<400> SEQUENCE: 65

```
Leu Asp Glu Arg Arg Leu Tyr Tyr Glu Gly Leu Gln
1               5                   10
```

<210> SEQ ID NO 66
<211> LENGTH: 12
<212> TYPE: PRT
<213> ORGANISM: Artificial
<220> FEATURE:
<223> OTHER INFORMATION: Synthetic peptide

<400> SEQUENCE: 66

```
Asp Glu Arg Arg Leu Tyr Tyr Glu Gly Leu Gln Asp
1               5                   10
```

<210> SEQ ID NO 67
<211> LENGTH: 12
<212> TYPE: PRT
<213> ORGANISM: Artificial
<220> FEATURE:
<223> OTHER INFORMATION: Synthetic peptide

<400> SEQUENCE: 67

```
Glu Arg Arg Leu Tyr Tyr Glu Gly Leu Gln Asp Lys
1               5                   10
```

<210> SEQ ID NO 68
<211> LENGTH: 12
<212> TYPE: PRT
<213> ORGANISM: Artificial
<220> FEATURE:
<223> OTHER INFORMATION: Synthetic peptide

<400> SEQUENCE: 68

```
Arg Arg Leu Tyr Tyr Glu Gly Leu Gln Asp Lys Leu
1               5                   10
```

<210> SEQ ID NO 69
<211> LENGTH: 12
<212> TYPE: PRT
<213> ORGANISM: Artificial
<220> FEATURE:
<223> OTHER INFORMATION: Synthetic peptide

<400> SEQUENCE: 69

```
Arg Leu Tyr Tyr Glu Gly Leu Gln Asp Lys Leu Ala
1               5                   10
```

<210> SEQ ID NO 70
<211> LENGTH: 12
<212> TYPE: PRT
<213> ORGANISM: Artificial
<220> FEATURE:
<223> OTHER INFORMATION: Synthetic peptide

<400> SEQUENCE: 70

```
Leu Tyr Tyr Glu Gly Leu Gln Asp Lys Leu Ala Gln
1               5                   10
```

<210> SEQ ID NO 71
<211> LENGTH: 12
<212> TYPE: PRT
<213> ORGANISM: Artificial
<220> FEATURE:
<223> OTHER INFORMATION: Synthetic peptide

<400> SEQUENCE: 71

Tyr Tyr Glu Gly Leu Gln Asp Lys Leu Ala Gln Ile

```
1               5                  10
```

<210> SEQ ID NO 72
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X stands for any amino acid

<400> SEQUENCE: 72

```
Xaa Arg Arg Leu Tyr Tyr Glu Gly Leu Gln Asp Lys
1               5                  10
```

<210> SEQ ID NO 73
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X stands for any amino acid

<400> SEQUENCE: 73

```
Glu Xaa Arg Leu Tyr Tyr Glu Gly Leu Gln Asp Lys
1               5                  10
```

<210> SEQ ID NO 74
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X stands for any amino acid

<400> SEQUENCE: 74

```
Glu Arg Xaa Leu Tyr Tyr Glu Gly Leu Gln Asp Lys
1               5                  10
```

<210> SEQ ID NO 75
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)

<400> SEQUENCE: 75

```
Glu Arg Arg Xaa Tyr Tyr Glu Gly Leu Gln Asp Lys
1               5                  10
```

<210> SEQ ID NO 76
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)

<223> OTHER INFORMATION: X stands for any amino acid

<400> SEQUENCE: 76

Glu Arg Arg Leu Xaa Tyr Glu Gly Leu Gln Asp Lys
1               5                   10

<210> SEQ ID NO 77
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X stands for any amino acid

<400> SEQUENCE: 77

Glu Arg Arg Leu Tyr Xaa Glu Gly Leu Gln Asp Lys
1               5                   10

<210> SEQ ID NO 78
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X stands for any amino acid

<400> SEQUENCE: 78

Glu Arg Arg Leu Tyr Tyr Xaa Gly Leu Gln Asp Lys
1               5                   10

<210> SEQ ID NO 79
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X stands for any amino acid

<400> SEQUENCE: 79

Glu Arg Arg Leu Tyr Tyr Glu Xaa Leu Gln Asp Lys
1               5                   10

<210> SEQ ID NO 80
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X stands for any amino acid

<400> SEQUENCE: 80

Glu Arg Arg Leu Tyr Tyr Glu Gly Xaa Gln Asp Lys
1               5                   10

<210> SEQ ID NO 81
<211> LENGTH: 12
<212> TYPE: PRT

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X stands for any amino acid

<400> SEQUENCE: 81

Glu Arg Arg Leu Tyr Tyr Glu Gly Leu Xaa Asp Lys
1               5                   10

<210> SEQ ID NO 82
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X stands for any amino acid

<400> SEQUENCE: 82

Glu Arg Arg Leu Tyr Tyr Glu Gly Leu Gln Xaa Lys
1               5                   10

<210> SEQ ID NO 83
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(12)

<400> SEQUENCE: 83

Glu Arg Arg Leu Tyr Tyr Glu Gly Leu Gln Asp Xaa
1               5                   10

<210> SEQ ID NO 84
<211> LENGTH: 12
<212> TYPE: PRT
<213> ORGANISM: Artificial
<220> FEATURE:
<223> OTHER INFORMATION: Synthetic peptide

<400> SEQUENCE: 84

Ala Arg Arg Leu Tyr Tyr Glu Gly Leu Gln Asp Lys
1               5                   10

<210> SEQ ID NO 85
<211> LENGTH: 12
<212> TYPE: PRT
<213> ORGANISM: Artificial
<220> FEATURE:
<223> OTHER INFORMATION: Synthetic peptide

<400> SEQUENCE: 85

Glu Ala Arg Leu Tyr Tyr Glu Gly Leu Gln Asp Lys
1               5                   10

<210> SEQ ID NO 86
<211> LENGTH: 12
<212> TYPE: PRT
<213> ORGANISM: Artificial
<220> FEATURE:
<223> OTHER INFORMATION: Synthetic peptide
```

<400> SEQUENCE: 86

Glu Arg Ala Leu Tyr Tyr Glu Gly Leu Gln Asp Lys
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic peptide

<400> SEQUENCE: 87

Glu Arg Arg Ala Tyr Tyr Glu Gly Leu Gln Asp Lys
1               5                   10

<210> SEQ ID NO 88
<211> LENGTH: 12
<212> TYPE: PRT
<213> ORGANISM: Artificial
<220> FEATURE:
<223> OTHER INFORMATION: Synthetic peptide

<400> SEQUENCE: 88

Glu Arg Arg Leu Ala Tyr Glu Gly Leu Gln Asp Lys
1               5                   10

<210> SEQ ID NO 89
<211> LENGTH: 12
<212> TYPE: PRT
<213> ORGANISM: Artificial
<220> FEATURE:
<223> OTHER INFORMATION: Synthetic peptide

<400> SEQUENCE: 89

Glu Arg Arg Leu Tyr Ala Glu Gly Leu Gln Asp Lys
1               5                   10

<210> SEQ ID NO 90
<211> LENGTH: 12
<212> TYPE: PRT
<213> ORGANISM: Artificial
<220> FEATURE:
<223> OTHER INFORMATION: Synthetic peptide

<400> SEQUENCE: 90

Glu Arg Arg Leu Tyr Tyr Ala Gly Leu Gln Asp Lys
1               5                   10

<210> SEQ ID NO 91
<211> LENGTH: 12
<212> TYPE: PRT
<213> ORGANISM: Artificial
<220> FEATURE:
<223> OTHER INFORMATION: Synthetic peptide

<400> SEQUENCE: 91

Glu Arg Arg Leu Tyr Tyr Glu Ala Leu Gln Asp Lys
1               5                   10

<210> SEQ ID NO 92
<211> LENGTH: 12
<212> TYPE: PRT
<213> ORGANISM: Artificial
<220> FEATURE:
<223> OTHER INFORMATION: Synthetic peptide

```
<400> SEQUENCE: 92

Glu Arg Arg Leu Tyr Tyr Glu Gly Ala Gln Asp Lys
1               5                   10

<210> SEQ ID NO 93
<211> LENGTH: 12
<212> TYPE: PRT
<213> ORGANISM: Artificial
<220> FEATURE:
<223> OTHER INFORMATION: Synthetic peptide

<400> SEQUENCE: 93

Glu Arg Arg Leu Tyr Tyr Glu Gly Leu Ala Asp Lys
1               5                   10

<210> SEQ ID NO 94
<211> LENGTH: 12
<212> TYPE: PRT
<213> ORGANISM: Artificial
<220> FEATURE:
<223> OTHER INFORMATION: Synthetic peptide

<400> SEQUENCE: 94

Glu Arg Arg Leu Tyr Tyr Glu Gly Leu Gln Ala Lys
1               5                   10

<210> SEQ ID NO 95
<211> LENGTH: 12
<212> TYPE: PRT
<213> ORGANISM: Artificial
<220> FEATURE:
<223> OTHER INFORMATION: Synthetic peptide

<400> SEQUENCE: 95

Glu Arg Arg Leu Tyr Tyr Glu Gly Leu Gln Asp Ala
1               5                   10

<210> SEQ ID NO 96
<211> LENGTH: 776
<212> TYPE: PRT
<213> ORGANISM: Rattus norvegicus

<400> SEQUENCE: 96

Met Gly Arg Gly Ser Gly Thr Phe Glu Arg Leu Leu Asp Lys Ala Thr
1               5                   10                  15

Ser Gln Leu Leu Leu Glu Thr Asp Trp Glu Ser Ile Leu Gln Ile Cys
                20                  25                  30

Asp Leu Ile Arg Gln Gly Asp Thr Gln Ala Lys Tyr Ala Val Asn Ser
            35                  40                  45

Ile Lys Lys Lys Val Asn Asp Lys Asn Pro His Val Ala Leu Tyr Ala
        50                  55                  60

Leu Glu Val Met Glu Ser Val Val Lys Asn Cys Gly Gln Thr Val His
65                  70                  75                  80

Asp Glu Val Ala Asn Lys Gln Thr Met Glu Leu Lys Glu Leu Leu
                85                  90                  95

Lys Arg Gln Val Glu Val Asn Val Arg Asn Lys Ile Leu Tyr Leu Ile
                100                 105                 110

Gln Ala Trp Ala His Ala Phe Arg Asn Glu Pro Lys Tyr Lys Val Val
            115                 120                 125

Gln Asp Thr Tyr Gln Ile Met Lys Val Glu Gly His Val Phe Pro Glu
        130                 135                 140
```

```
Phe Lys Glu Ser Asp Ala Met Phe Ala Ala Glu Arg Ala Pro Asp Trp
145                 150                 155                 160

Val Asp Ala Glu Glu Cys His Arg Cys Arg Val Gln Phe Gly Val Val
                165                 170                 175

Thr Arg Lys His His Cys Arg Ala Cys Gly Gln Ile Phe Cys Gly Lys
                180                 185                 190

Cys Ser Ser Lys Tyr Ser Thr Ile Pro Lys Phe Gly Ile Glu Lys Glu
            195                 200                 205

Val Arg Val Cys Glu Pro Cys Tyr Glu Gln Leu Asn Lys Lys Ala Glu
        210                 215                 220

Gly Lys Ala Ala Ser Thr Thr Glu Leu Pro Pro Glu Tyr Leu Thr Ser
225                 230                 235                 240

Pro Leu Ser Gln Gln Ser Gln Leu Pro Pro Lys Arg Asp Glu Thr Ala
                245                 250                 255

Leu Gln Glu Glu Glu Glu Leu Gln Leu Ala Leu Ala Leu Ser Gln Ser
                260                 265                 270

Glu Ala Glu Glu Lys Glu Arg Met Arg Gln Lys Ser Thr Tyr Thr Ala
                275                 280                 285

His Pro Lys Ser Glu Pro Ala Pro Leu Ala Ser Ser Ala Pro Pro Ala
            290                 295                 300

Gly Ser Leu Tyr Ser Ser Pro Val Asn Ser Ser Ala Pro Leu Ala Glu
305                 310                 315                 320

Asp Ile Asp Pro Glu Leu Ala Arg Tyr Leu Asn Arg Asn Tyr Trp Glu
                325                 330                 335

Lys Lys Gln Glu Glu Ala Arg Lys Ser Pro Thr Pro Ser Ala Pro Val
                340                 345                 350

Pro Leu Thr Glu Pro Ala Ala Gln Pro Gly Glu Gly His Thr Ala Pro
                355                 360                 365

Asn Ser Met Val Glu Ala Pro Leu Pro Glu Thr Asp Ser Gln Pro Ile
            370                 375                 380

Thr Ser Cys Ser Gly Pro Phe Ser Glu Gln Tyr Gln Asn Gly Glu Ser
385                 390                 395                 400

Glu Glu Ser His Glu Gln Phe Leu Lys Ala Leu Gln Asn Ala Val Ser
                405                 410                 415

Thr Phe Val Asn Arg Met Lys Ser Asn His Met Arg Gly Arg Ser Ile
            420                 425                 430

Thr Asn Asp Ser Ala Val Leu Ser Leu Phe Gln Ser Ile Asn Ser Thr
            435                 440                 445

His Pro Gln Leu Leu Glu Leu Leu Asn Arg Leu Asp Glu Arg Arg Leu
450                 455                 460

Tyr Tyr Glu Gly Leu Gln Asp Lys Leu Ala Gln Ile Arg Asp Ala Arg
465                 470                 475                 480

Gly Ala Leu Ser Ala Leu Arg Glu Glu His Arg Glu Lys Leu Arg Arg
                485                 490                 495

Ala Ala Glu Glu Ala Glu Arg Gln Arg Gln Ile Gln Leu Ala Gln Lys
                500                 505                 510

Leu Glu Ile Met Arg Gln Lys Lys Gln Glu Tyr Leu Glu Val Gln Arg
            515                 520                 525

Gln Leu Ala Ile Gln Arg Leu Gln Glu Gln Lys Glu Arg Gln Met
            530                 535                 540

Arg Leu Glu Gln Gln Lys Gln Thr Val Gln Met Arg Ala Gln Met Pro
545                 550                 555                 560

Ala Phe Pro Leu Pro Tyr Ala Gln Leu Gln Ala Met Pro Thr Ala Gly
```

-continued

```
            565                 570                 575
Gly Val Leu Tyr Gln Pro Ser Gly Pro Thr Ser Phe Pro Gly Thr Phe
            580                 585                 590

Ser Pro Ala Gly Ser Val Glu Gly Ser Pro Met His Gly Val Tyr Met
            595                 600                 605

Ser Gln Pro Ala Pro Ala Thr Gly Pro Tyr Pro Ser Met Pro Gly Thr
            610                 615                 620

Thr Ala Asp Pro Ser Met Val Ser Ala Tyr Met Tyr Pro Ala Gly Ala
625                 630                 635                 640

Pro Gly Ala Gln Ala Ala Pro Gln Ala Gln Ala Gly Pro Thr Thr Asn
                645                 650                 655

Pro Ala Tyr Ser Ser Tyr Gln Pro Thr Pro Thr Pro Gly Tyr Gln Asn
                660                 665                 670

Val Ala Ser Gln Ala Pro Gln Ser Leu Pro Ala Ile Ser Gln Pro Pro
                675                 680                 685

Gln Thr Ser Asn Ile Gly Tyr Met Gly Ser Gln Pro Met Ser Met Gly
            690                 695                 700

Tyr Gln Pro Tyr Asn Met Gln Asn Leu Met Thr Thr Leu Pro Gly Gln
705                 710                 715                 720

Asp Ala Ser Leu Pro Ala Gln Gln Pro Tyr Ile Thr Gly Gln Gln Pro
                725                 730                 735

Met Tyr Gln Gln Met Ala Pro Ser Thr Gly Pro Pro Gln Gln Gln Pro
                740                 745                 750

Pro Val Ala Gln Pro Pro Thr Gln Gly Pro Pro Ala Gln Gly Asn
                755                 760                 765

Glu Thr Gln Leu Ile Ser Phe Asp
770                 775
```

ANTITUMOR AGENT TARGETING HGF-REGULATED TYROSINE KINASE SUBSTRATE (HGS)

TECHNICAL FIELD

The present invention relates to an antitumor agent targeting HGF-regulated tyrosine kinase substrate (HGS).

BACKGROUND ART

Hepatocyte growth factor-regulated tyrosine kinase substrate (HGS) forms a complex with signal-transducing adaptor molecule (STAM) and is a constituent molecule of the Endosomal Sorting Complexes Required for Transport (ES-CRT) which is responsible for endosomal intraluminal vesicle formation (multivesicular body formation). HGS is also called Hrs.

The expression level of HGS is known to increase in cancer cells, and high expression of HGS is known to promote cancer cell metastasis, angiogenesis, and cancer cell growth. On the other hand, it is known that, when the coiled-coil region of HGS (hereinafter also referred to as "C region" or "HGS/C") or a partial peptide thereof is highly expressed in cancer cells, they inhibit angiogenesis and cancer cell growth (Patent Literature 1: International Publication No. WO 2011/162419).

CITATION LIST

Patent Literature

[Patent Literature 1] International Publication No. WO 2011/162419

SUMMARY OF INVENTION

Technical Problem

As described above, the partial peptide of the C region of HGS inhibits tumor growth. However, a peptide having a higher tumor growth inhibitory effect is desired for use as an antitumor agent.

Solution to Problem

As a result of intensive research to solve the above problem, the present inventor has succeeded in producing a peptide having a higher tumor growth inhibitory effect as compared with conventional partial peptides of HGS/C, and completed the present invention.

That is, the present invention is as follows.

(1) An antitumor agent comprising a peptide comprising at least 10 consecutive amino acid residues of an amino acid sequence of the C region of HGF-regulated tyrosine kinase substrate (HGS), excepting peptides consisting of any of the amino acid sequences of SEQ ID NOs: 13 to 34.

(2) The antitumor agent according to (1), wherein the peptide is the following (a), (b) or (c):

(a) a peptide consisting of the amino acid sequence of SEQ ID NO: 67;

(b) a peptide consisting of an amino acid sequence in which one or several amino acids are deleted, substituted or added in the peptide consisting of the amino acid sequence of SEQ ID NO: 67, and having a tumor growth inhibitory effect or a metastasis inhibitory effect; or (c) a peptide having 80% or more sequence identity with the peptide consisting of the amino acid sequence of SEQ ID NO: 67, and having a tumor growth inhibitory effect or a metastasis inhibitory effect.

(3) The antitumor agent according to (1), wherein the peptide is the following (d), (e) or (f):

(d) a peptide consisting of the amino acid sequence of SEQ ID NO: 50;

(e) a peptide consisting of an amino acid sequence in which one or several amino acids are deleted, substituted or added in the peptide consisting of the amino acid sequence of SEQ ID NO: 50, and having a tumor growth inhibitory effect or a metastasis inhibitory effect; or (f) a peptide having 80% or more sequence identity with the peptide consisting of the amino acid sequence of SEQ ID NO: 50, and having a tumor growth inhibitory effect or a metastasis inhibitory effect.

(4) The antitumor agent according to (1), wherein the peptide is the following (g), (h) or (i):

(g) a peptide consisting of the amino acid sequence of SEQ ID NO: 59;

(h) a peptide consisting of an amino acid sequence in which one or several amino acids are deleted, substituted or added in the peptide consisting of the amino acid sequence of SEQ ID NO: 59, and having a tumor growth inhibitory effect or a metastasis inhibitory effect; or (i) a peptide having 80% or more sequence identity with the peptide consisting of the amino acid sequence of SEQ ID NO: 59, and having a tumor growth inhibitory effect or a metastasis inhibitory effect.

(5) The antitumor agent according to (2), wherein the peptide is a peptide consisting of any of the following amino acid sequences (j) to (p) (wherein X represents an arbitrary amino acid), and having a tumor growth inhibitory effect or a metastasis inhibitory effect:

```
                                        (SEQ ID No. 73)
(j)  E-X-R-L-Y-Y-E-G-L-Q-D-K (SEQ ID No. 74)
(k)  E-R-X-L-Y-Y-E-G-L-Q-D-K (SEQ ID No. 75)
(l)  E-R-R-X-Y-Y-E-G-L-Q-D-K (SEQ ID No. 76)
(m)  E-R-R-L-X-Y-E-G-L-Q-D-K (SEQ ID No. 79)
(n)  E-R-R-L-Y-Y-E-X-L-Q-D-K (SEQ ID No. 80)
(o)  E-R-R-L-Y-Y-E-G-X-Q-D-K (SEQ ID No. 81)
(p)  E-R-R-L-Y-Y-E-G-L-X-D-K.
```

(6) The antitumor agent according to any one of (1) to (5), which is a tumor growth inhibitor.

(7) The antitumor agent according to any one of (1) to (5), which is a metastasis inhibitor.

(8) A method for treating a cancer or tumor in a subject, which comprises administering a therapeutically effective amount of a peptide to the subject, wherein the peptide is a peptide comprising at least 10 consecutive amino acid residues of an amino acid sequence of the C region of HGF-regulated tyrosine kinase substrate (HGS), excepting peptides consisting of the amino acid sequences of SEQ ID NOs: 13-34.

(9) A method for inhibiting growth or metastasis of a cancer or tumor in a subject, which comprises administering an effective amount of a peptide to the subject, wherein the peptide is a peptide comprising at least 10 consecutive amino acid residues of an amino acid sequence of the C region of HGF-regulated tyrosine kinase substrate (HGS), excepting peptides consisting of the amino acid sequences of SEQ ID NOs: 13-34.

(10) A peptide comprising at least 10 consecutive amino acid residues of an amino acid sequence of the C region of HGF-regulated tyrosine kinase substrate (HGS), excepting peptides consisting of the amino acid sequences of SEQ ID NOs: 13-34, for use in treatment of a cancer or tumor.

(11) A peptide comprising at least 10 consecutive amino acid residues of an amino acid sequence of the C region of HGF-regulated tyrosine kinase substrate (HGS), excepting peptides consisting of the amino acid sequences of SEQ ID NOs: 13-34, for use in inhibiting growth or metastasis of a cancer or tumor.

Effects of Invention

According to the present invention, it is possible to provide a peptide having a higher tumor growth inhibitory effect as compared with conventional partial peptides of HGS/C and an antitumor agent comprising the same.

BRIEF DESCRIPTION OF DRAWINGS

FIG. 1 is a schematic diagram showing the structure of HGS.

FIG. 2A is a diagram showing the results of an anchorage-independent/dependent growth inhibition test in B16 cells.

FIG. 2B is a diagram showing the results of an anchorage-independent/dependent growth inhibition test in COLO 205 cells.

FIG. 3A is a diagram showing the results of an in vivo Xenograft test using an oligopeptide of the present invention (OP12-462).

FIG. 3B is a diagram showing the results of an in vivo Xenograft test using an oligopeptide of the present invention (OP10-507).

FIG. 3C is a diagram showing the results of an in vivo Xenograft test using an oligopeptide of the present invention (OP10-527).

FIG. 4 is a diagram showing the results of an experimental lung metastasis inhibition test using an oligopeptide of the present invention (OP12-462).

FIG. 5 is a diagram showing the results of an anchorage-independent growth inhibition test using a mutant of an oligopeptide of the present invention (OP12-462).

FIG. 6A is a diagram showing the results of an in vivo Xenograft test using a conventional oligopeptide (OP10-10).

FIG. 6B is a diagram showing the results of an in vivo Xenograft test using a conventional oligopeptide (OP10-7).

FIG. 6C is a diagram showing the results of an in vivo Xenograft test using a conventional oligopeptide (OP10-11).

DESCRIPTION OF EMBODIMENTS

The following describes in detail the present invention. The following embodiments are examples for explaining the present invention, and are not intended to limit the present invention only to these embodiments. The present invention can be implemented in various forms as long as it does not deviate from the gist thereof. In addition, the present description includes the contents described in the description and drawings of the Japanese patent application (Japanese Patent Application No. 2018-160501) filed on Aug. 29, 2018, which serves as the basis for the right of priority of the present application.

1. Overview

The present invention relates to an antitumor agent targeting HGF-regulated tyrosine kinase substrate (HGS).

Conventionally, the partial peptide of the C region of HGS has been known to inhibit tumor growth (International Publication No. WO 2011/162419). However, at present, a peptide having a higher tumor growth inhibitory effect is needed for use as an antitumor agent.

Therefore, as a result of intensive research, the present inventor has found a peptide having a higher tumor growth inhibitory effect as compared with conventional partial peptides of HGS/C, and completed the present invention.

2. HGS (1) Functions of HGS

HGS forms a complex with signal-transducing adaptor molecule (STAM) and is a constituent molecule of the Endosomal Sorting Complexes Required for Transport (ES-CRT) which is responsible for endosomal intraluminal vesicle formation (multivesicular body formation). Wnt-β-catenin signaling is induced by multivesicular body formation, and this signal causes tumor growth, epithelial-mesenchymal transition (EMT) and the like. EMT is an essential process in early embryonic morphogenesis and is also greatly involved in invasion and penetration into blood vessels in cancer cell metastasis.

(2) HGS

In the present invention, the animal species from which HGS is derived is not limited, and it may be derived from rats, humans, or mice. Rat HGS is a homologue of mouse or human HGS. The amino acid sequence homologies (identities) between rat HGS and mouse HGS, rat HGS and human HGS, and mouse HGS and human HGS are as follows.

(a) Amino acid sequence homology between rat HGS and mouse HGS is 97%

(b) Amino acid sequence homology between rat HGS and human HGS is 93%

(c) Amino acid sequence homology between mouse HGS and human HGS is 93%

Therefore, in the present invention, HGS includes rat-derived HGS, human-derived HGS, and mouse-derived HGS.

The amino acid sequences of HGS derived from rats, humans, and mice are represented by SEQ ID NOs: 2, 4, and 6, respectively. In addition, the base sequences of the polynucleotides encoding HGS derived from rats, humans, and mice are represented by SEQ ID NOs: 1, 3, and 5, respectively. The above base sequences and amino acid sequences are registered in GenBank. The GenBank accession numbers of the base sequences and amino acid sequences of various HGS (Hrs) are shown below.

Rat HGS (SEQ ID NOs: 1 and 2): AB002811
Human HGS (SEQ ID NOs: 3 and 4): U43895
Mouse HGS (SEQ ID NOs: 5 and 6): D50050

In addition, in the present invention, the amino acid sequence of SEQ ID NO: 96 can be used as the amino acid sequence of rat HGS.

(3) Polynucleotides Encoding HGS

As described above, rat HGS is a homologue of mouse or human HGS. Therefore, the polynucleotides encoding HGS of the present invention include polynucleotides encoding HGS, such as the polynucleotides encoding human or mouse HGS (SEQ ID NO: 3 or 5), and the polynucleotides encoding the human or mouse HGS peptide consisting of the amino acid sequence of SEQ ID NO: 4 or 6. In addition, the polynucleotides encoding HGS of the present invention also include the polynucleotides encoding rat HGS.

Here, "polynucleotide" refers to a polymer consisting of a plurality of bases or base pairs such as deoxyribonucleic acid (DNA) or ribonucleic acid (RNA), and includes DNA, cDNA, genomic DNA, chemically synthesized DNA and RNA. In addition, polynucleotides comprising non-natural artificial bases as needed are also included to the polynucleotide of the present invention.

3. C Region of HGS (1) C Region of HGS

As shown in FIG. 1, the HGS protein is a protein composed of four regions (domains) in order from the amino terminal end: a region (Z) having a zinc-finger sequence (FYVE), a proline-rich region (P), a coiled-coil region (C), and a proline-rich/glutamine-rich region (Q).

The peptides comprising at least the C-Q regions of HGS have the ability to induce EMT, and the peptides comprising no Q region but comprising the C region (for example, ZPC, PC, and C) have inhibitory activity against EMT induction. In addition, in in vitro cell migration experiments using a Transwell chamber, cells expressing full-length HGS (ZPCQ) have increased migration properties, whereas in HGS mutants (ZPC, PC, and C) lacking the Q region but comprising the C region, their migration properties are remarkably reduced, and in particular, the cells expressing the C region have remarkably reduced migration properties (Japanese Patent Laid-Open No. 2005-247735). Furthermore, the peptides of the C region of HGS inhibit the metastasis of cancer cells.

Therefore, the peptides of the C region of HGS have a cancer metastasis inhibitory effect. Moreover, the peptides of the C region of HGS have a tumor growth inhibitory effect.

(2) Peptides Comprising C Region of HGS

In the present invention, the peptides of HGS/C and mutants thereof can be easily prepared by those skilled in the art based on Table 1 below and the method for preparing a mutant described later. The positions of the Z, P, C and Q regions in the amino acid sequences represented by SEQ ID NO: 2, SEQ ID NO: 4 and SEQ ID NO: 6 are shown in Table 1 below.

TABLE 1

Positions of Z, P, C and Q regions in full-length HGS amino acid sequence

|  | Z | P | C | Q |
|---|---|---|---|---|
| Rat (SEQ ID NO: 2) | 1~233 | 234~390 | 391~562 | 563~771 |
| Human (SEQ ID NO: 4) | 1~233 | 234~390 | 391~563 | 564~777 |
| Mouse (SEQ ID NO: 6) | 1~233 | 234~390 | 391~561 | 562~775 |

In the present invention, examples of the peptides of the C region of HGS include peptides consisting of the amino acid sequence represented by SEQ ID NO: 8 (rat HGS/C), SEQ ID NO: 10 (human HGS/C) or SEQ ID NO: 12 (mouse HGS/C).

(3) Polynucleotides Encoding Peptides Comprising the C Region of HGS

Examples of the polynucleotides encoding the peptides described in the above (2) include polynucleotides encoding HGS/C. These polynucleotides and mutants thereof can be easily prepared by those skilled in the art based on Table 2 below and known hybridization methods. The positions of the Z, P, C and Q regions in the base sequences of SEQ ID NO: 1 (rat HGS), SEQ ID NO: 3 (human HGS) and SEQ ID NO: 5 (mouse HGS) are shown in Table 2 below.

TABLE 2

Positions of polynucleotides encoding Z, P, C and Q regions

|  | Z | P | C | Q |
|---|---|---|---|---|
| Rat (SEQ ID NO: 1) | 21~719 | 720~1190 | 1191~1706 | 1707~2333 |
| Human (SEQ ID NO: 3) | 76~774 | 775~1245 | 1246~1764 | 1765~2406 |
| Mouse (SEQ ID NO: 5) | 43~741 | 742~1212 | 1213~1725 | 1726~2367 |

In the present invention, the polynucleotides encoding HGS/C are not limited as long as they are a polynucleotide comprising the base sequence represented by SEQ ID NO: 7, 9 or 11, or the bases sequences encoding the C region peptide of HGS. For example, in addition to a polynucleotide encoding the peptide consisting of the amino acid sequence represented by SEQ ID NO: 8, 10 or 12, a polynucleotide encoding a mutant peptide consisting of an amino acid sequence in which one or more amino acids are deleted, inserted, substituted or added in the amino acid sequence represented by SEQ ID NO: 8, 10 or 12, and having a tumor growth inhibitory effect or a metastasis inhibitory effect, can also be used in the present invention.

The polynucleotides encoding HGS/C of the present invention include a polynucleotide consisting of the base sequence represented by SEQ ID NO: 7, 9 or 11, or a polynucleotide hybridizing with a polynucleotide consisting of a sequence complementary to the base sequence represented by SEQ ID NO: 7, 9 or 11 under stringent conditions, and encoding a peptide having a tumor growth inhibitory effect or a metastasis inhibitory effect. Such a polynucleotide can be obtained with a known method based on the polynucleotide consisting of the base sequence represented by SEQ ID NO: 7, 9 or 11.

4. Constituent Oligopeptides of the C Region of HGS (HGS/C Constituent Oligopeptides)

Some of the peptides of the C region of HGS also have an inhibitory effect on cancer cell metastasis and a tumor growth inhibitory effect. For example, as described in the Examples below, the constituent oligopeptides of the C region of HGS have an inhibitory effect on cancer cell metastasis and a tumor growth inhibitory effect.

The peptides of the C region of HGS are proteins of about 30 kD, which were not easy to mass-produce. However, the constituent oligopeptides of the C region of HGS are peptides of 1.5 kD or less, and are easy to produce.

Therefore, the peptides used in the present invention include peptides comprising a part of the C region of HGS. Here, the length of the amino acid sequence of the "part" is not limited as long as it is a length comprising at least 10 consecutive amino acid residues. That is, in the present invention, the peptides comprising a part of the C region of HGS include a "peptide comprising at least 10 consecutive amino acid residues of the amino acid sequence of the C region of HGS". In addition, the "peptide" in the present invention also includes oligopeptides having 2 to 20 amino acid residues and polypeptides having 20 or more amino acid residues.

However, the peptides consisting of the following amino acid sequences are not included in the peptides used in the present invention (excluded from the peptides used in the present invention).

```
                                        (SEQ ID No. 13)
OP20-1: MKSNHMRGRSITNDSAVLSL (SEQ ID No. 14)
OP20-2: ITNDSAVLSLFQSINTMHPQ (SEQ ID No. 15)
OP20-3: FQSINTMHPQLLELLNQLDE (SEQ ID No. 16)
OP20-4: LLELLNQLDERRLYYEGLQD (SEQ ID No. 17)
OP20-5: RRLYYEGLQDKLAQIRDARG (SEQ ID No. 18)
OP20-6: KLAQIRDARGALSALREEHR (SEQ ID No. 19)
OP20-7: ALSALREEHREKLRRAAEEA (SEQ ID No. 20)
OP20-8: EKLRRAAEEAERQRQIQLAQ (SEQ ID No. 21)
OP20-9: ERQRQIQLAQKLEIMRQKKQ (SEQ ID No. 22)
OP20-10: KLEIMRQKKQEYLEVQRQLA (SEQ ID No. 23)
OP20-11: EYLEVQRQLAIQRLQEQEKE (SEQ ID No. 24)
OP20-12: IQRLQEQEKERQMRLEQQKQ (SEQ ID No. 25)
OP20-13: RQMRLEQQKQTVQMRAQMPA (SEQ ID No. 26)
OP10-1: MGRGSGTFER (SEQ ID No. 27)
OP10-3: FQSINTMHPQ (SEQ ID No. 28)
OP10-6: KLAQIRDARG (SEQ ID No. 29)
OP10-7: ALSALREEHR (SEQ ID No. 30)
OP10-8: EKLRRAAEEA (SEQ ID No. 31)
OP10-9: ERQRQIQLAQ (SEQ ID No. 32)
OP10-10: KLEIMRQKKQ (SEQ ID No. 33)
OP10-11: EYLEVQRQLA (SEQ ID No. 34)
OP10-12: IQRLQEQEKE
```

In the present invention, examples of the "peptide comprising at least 10 consecutive amino acid residues of the amino acid sequence of the C region of HGS" include peptides comprising at least 10 consecutive amino acid residues or more, 11 consecutive amino acid residues or more, 12 consecutive amino acid residues or more, 14 consecutive amino acid residues or more of the amino acid sequence of SEQ ID NO: 8, 10 or 12. More specifically, peptides comprising 10 to 30 consecutive amino acid residues, preferably 10 to 20 consecutive amino acid residues, more preferably 10 to 14 consecutive amino acid residues, further preferably 10 to 12 consecutive amino acid residues of the amino acid sequence of SEQ ID NO: 8, 10 or 12 are included.

In addition, the range of the amino acid sequence in which the amino acid sequence of "at least 10 consecutive amino acid residues of the amino acid sequence of the C region of HGS" is selected is not limited as long as it is within the range of the amino acid sequence of SEQ ID NO: 8, 10 or 12 (the amino acid sequence of from 391st to 562nd amino acid, the amino acid sequence of from 391st to 563rd amino acid or the amino acid sequence of from 391st to 561st amino acid in the amino acid sequence of SEQ ID NO: 2, 4, or 6), but examples thereof include the range of the following amino acid sequences:

an amino acid sequence of from 407th (Q (glutamine)) to 560th (M (methionine)) amino acid, an amino acid sequence of from 407th (Q) to 551st (K (lysine)) amino acid, an amino acid sequence of from 407th (Q) to 479th (D (aspartic acid)) amino acid, an amino acid sequence of from 420th (V (valine)) to 560th (M) amino acid, an amino acid sequence of from 420th (V) to 551st (K) amino acid, an amino acid sequence of from 420th (V) to 479th (D) amino acid, an amino acid sequence of from 443rd (F (phenylalanine)) to 560th (M) amino acid, an amino acid sequence of from 443rd (F) to 551st (K) amino acid, an amino acid sequence of from 443rd (F) to 479th (D) amino acid, an amino acid sequence of from 452nd (Q (glutamine)) to 560th (M) amino acid, an amino acid sequence of from 452nd (Q) to 551st (K) amino acid, an amino acid sequence of from 452nd (Q) to 479th (D) amino acid, an amino acid sequence of from 479th (D) to 560th (M) amino acid, and an amino acid sequence of from 479th (M) to 551st (K) amino acid in the amino acid sequence of SEQ ID NO: 4.

The range of the amino acid sequence in which the amino acid sequence of "at least 10 consecutive amino acid residues of the amino acid sequence of the C region of HGS" is selected is preferably the amino acid sequence of from 407th (Q) to 560th (M) amino acid, more preferably the amino acid sequence of from 407th (Q) to 551st (K) amino acid, the amino acid sequence of from 420th (V) to 560th (M) amino acid, the amino acid sequence of from 443rd (F) to the 560th (M) amino acid or the amino acid sequence of from 452nd (Q) to 560th (M) amino acid, further preferably the amino acid sequence of from 420th (V) to 551st (K) amino acid or the amino acid sequence of from 443rd (F) to 551st (K) amino acid, and furthermore preferably the amino acid sequence of from 452nd (Q) to 551st (K) amino acid in the amino acid sequence of SEQ ID NO: 4.

In another aspect, the range of the amino acid sequence in which the amino acid sequence of "at least 10 consecutive amino acid residues of the amino acid sequence of the C region of HGS" is selected is preferably the amino acid sequence of from 407th (Q) to 479th (D) amino acid, more preferably the amino acid sequence of from 420th (V) to 479th (D) amino acid, further preferably the amino acid sequence of from 443rd (F) to 479th (D) amino acid, and furthermore preferably the amino acid sequence of from 452nd (Q) to 479th (D) amino acid in the amino acid sequence of SEQ ID NO: 4.

In another aspect, the range of the amino acid sequence in which the amino acid sequence of "at least 10 consecutive amino acid residues of the amino acid sequence of the C region of HGS" is selected is preferably the amino acid sequence of from 479th (D) to 560th (M) amino acid, and more preferably the amino acid sequence of from 479th (D) to 551st (K) amino acid in the amino acid sequence of SEQ ID NO: 4.

Similarly, in the amino acid sequences of SEQ ID NOs: 2 and 6, a range of the amino acid sequences corresponding to the range of the above amino acid sequences in the amino acid sequence of SEQ ID NO: 4 can be selected as the amino acid sequence of "at least 10 consecutive amino acid residues of the amino acid sequence of the C region of HGS".

Furthermore, the amino acid sequence of "at least 10 consecutive amino acid residues of the amino acid sequence of the C region of HGS" is not limited, and examples thereof include the amino acid sequences comprising any of the amino acid sequences shown in the table below. The amino acid sequence preferably comprises any of the amino acid sequences OP10-463 (SEQ ID NO: 38), OP10-507 (SEQ ID NO: 50), OP10-527 (SEQ ID NO: 59) and OP12-462 (SEQ ID NO: 67).

TABLE 3

| Code name | Amino acid sequence | SEQ ID NO |
|---|---|---|
| OP10-460 | LDERRLYYEG | 35 |
| OP10-461 | DERRLYYEGL | 36 |
| OP10-462 | ERRLYYEGLQ | 37 |
| OP10-463 | RRLYYEGLQD | 38 |
| OP10-464 | RLYYEGLQDK | 39 |
| OP10-465 | LYYEGLQDKL | 40 |
| OP10-466 | YYEGLQDKLA | 41 |
| OP10-467 | YEGLQDKLAQ | 42 |
| OP10-468 | EGLQDKLAQI | 43 |
| OP10-469 | GLQDKLAQIR | 44 |
| OP10-470 | LQDKLAQIRD | 45 |
| . . . | | |
| OP10-503 | ERQRQIQLAQ | 46 |
| OP10-504 | RQRQIQLAQK | 47 |
| OP10-505 | QRQIQLAQKL | 48 |
| OP10-506 | RQIQLAQKLE | 49 |
| OP10-507 | QIQLAQKLEI | 50 |
| OP10-508 | IQLAQKLEIM | 51 |
| OP10-509 | QLAQKLEIMR | 52 |
| OP10-510 | LAQKLEIMRQ | 53 |
| OP10-511 | AQKLEIMRQK | 54 |
| . . . | | |

TABLE 3-continued

| Code name | Amino acid sequence | SEQ ID NO |
|---|---|---|
| OP10-523 | EYLEVQRQLA | 55 |
| OP10-524 | YLEVQRQLAI | 56 |
| OP10-525 | LEVQRQLAIQ | 57 |
| OP10-526 | EVQRQLAIQR | 58 |
| OP10-527 | VQRQLAIQRL | 59 |
| OP10-528 | QRQLAIQRLQ | 60 |
| OP10-529 | RQLAIQRLQE | 61 |
| OP10-530 | QLAIQRLQEQ | 62 |
| OP10-531 | LAIQRLQEQE | 63 |
| OP10-532 | AIQRLQEQEK | 64 |

TABLE 4

| Code name | Amino acid sequence | SEQ ID NO |
|---|---|---|
| OP12-460 | LDERRLYYEGLQ | 65 |
| OP12-461 | DERRLYYEGLQD | 66 |
| OP12-462 | ERRLYYEGLQDK | 67 |
| OP12-463 | RRLYYEGLQDKL | 68 |
| OP12-464 | RLYYEGLQDKLA | 69 |
| OP12-465 | LYYEGLQDKLAQ | 70 |
| OP12-466 | YYEGLQDKLAQI | 71 |

In addition, the "peptide comprising at least 10 consecutive amino acid residues of the amino acid sequence of the C region of HGS" includes peptides consisting of an amino acid sequence in which one or several amino acids are deleted, substituted or added or mutated by a combination thereof in the amino acid sequence comprising at least 10 consecutive amino acid residues of the amino acid sequence of SEQ ID NO: 8, 10 or 12, and having a tumor growth inhibitory effect or a metastasis inhibitory effect. Here, "several" means 1 to 10 (for example, 1 to 5, preferably 1 to 3, more preferably 1 to 2, further preferably 1). When the total number of amino acid residues comprised in the peptide is around 20, it means 1 to 5, and when the total number of amino acid residues comprised in the peptide is around 10, it means 1 to 3.

The "peptide comprising at least 10 consecutive amino acid residues of the amino acid sequence of the C region of HGS" includes peptides consisting of "at least 10 consecutive amino acid residues of the amino acid sequence of the C region of HGS" or mutants thereof to which a cell-penetrating peptide is added (bound).

In addition, the "peptide comprising at least 10 consecutive amino acid residues of the amino acid sequence of the C region of HGS" include cyclic peptides consisting of an amino acid sequence of "at least 10 consecutive amino acid residues of the amino acid sequence of the C region of HGS".

The HGS/C constituent oligopeptides used in the present invention include oligopeptides consisting of the amino acid sequence of SEQ ID NO: 38, 50, 59 or 67, as well as peptides consisting of an amino acid sequence in which one or several amino acids are deleted, substituted or added or mutated by a combination thereof in the amino acid sequence of SEQ ID NO: 38, 50, 59 or 67, and having a tumor growth inhibitory effect or a metastasis inhibitory effect.

Examples of amino acid sequences in which one or several amino acids are deleted, substituted or added or mutated by a combination thereof in the amino acid sequence of SEQ ID NO: 38, 50, 59 or 67 include:

(i) an amino acid sequence in which 1 to 10 (for example, 1 to 5, preferably 1 to 3, more preferably 1 to 2, further preferably 1) amino acids in the amino acid sequence of SEQ ID NO: 38, 50, 59 or 67 are deleted;

(ii) an amino acid sequence in which 1 to 10 (for example, 1 to 5, preferably 1 to 3, more preferably 1 to 2, further preferably 1) amino acids in the amino acid sequence of SEQ ID NO: 38, 50, 59 or 67 are substituted with other amino acids;

(iii) an amino acid sequence in which 1 to 10 (for example, 1 to 5, preferably 1 to 3, more preferably 1 to 2, further preferably 1) amino acids are added to the amino acid sequence of SEQ ID NO: 38, 50, 59 or 67;

(iv) an amino acid sequence mutated by the combination of (i) to (iii).

In the present invention, the "tumor growth inhibitory effect" means the effect of inhibiting the growth of cancer cells. Moreover, the "metastasis inhibitory effect" means the effect of inhibiting the migration of cancer cells.

In addition, "having a tumor growth inhibitory effect or a metastasis inhibitory effect" means having an activity of 10% or more, 20% or more, 30% or more, 40% or more, 50% or more, 60% or more, 70% or more, 80% or more, preferably 90% or more, compared to when the tumor growth inhibitory effect or metastasis inhibitory effect of the peptide having the amino acid sequence of SEQ ID NO: 38, 50, 59 or 67 is 100%.

The tumor growth inhibitory effect can be measured by expressing a mutant peptide in any cancer cell and measuring the amount of tumor growth using a known method. In addition, the metastasis inhibitory effect can be confirmed by the experimental lung metastasis inhibition test described in the Examples below or the like.

The introduction of a mutation into a polynucleotide to prepare a peptide having the above mutations can be performed using a mutagenesis kit utilizing a site-directed mutagenesis method such as the Kunkel method or the Gapped duplex method, for example, QuikChange™ Site-Directed Mutagenesis Kit (manufactured by Stratagene), GeneTailor™ Site-Directed Mutagenesis System (manufactured by Invitrogen), TaKaRa Site-Directed Mutagenesis System (Mutan-K, Mutan-Super Express Km, etc.: manufactured by Takara Bio), and the like. In addition, a method such as the site-directed mutagenesis methods described in "Molecular Cloning, A Laboratory Manual 2nd ed." (Cold Spring Harbor Press (1989)), "Current Protocols in Molecular Biology" (John Wiley & Sons (1987-1997)), Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6, and the like can be used.

Moreover, the HGS/C constituent oligopeptides used in the present invention also include the amino acid sequence of SEQ ID NO: 38, 50, 59 or 67, as well as those having an amino acid sequence having about 80% or more, about 81% or more, about 82% or more, preferably about 90% or more, about 91% or more, about 92% or more identity with the amino acid sequence of SEQ ID NO: 38, 50, 59 or 67, and having a tumor growth inhibitory effect or a metastasis inhibitory effect (amino acid sequences substantially equivalent to the amino acid sequence of SEQ ID NO: 38, 50, 59 or 67). For homology (identity), homology searches such as FASTA, BLAST, PSI-BLAST can be used at a homology search site using the Internet, for example, the DNA Data Bank of Japan (DDBJ). In addition, a search using BLAST can also be performed at the National Center for Biotechnology Information (NCBI).

Furthermore, examples of HGS/C constituent oligopeptides include peptides consisting of any of the following amino acid sequences (wherein X represents an arbitrary amino acid), and having a tumor growth inhibitory effect or a metastasis inhibitory effect:

```
                                       (SEQ ID No. 72)
X-R-R-L-Y-Y-E-G-L-Q-D-K (SEQ ID No. 73)
E-X-R-L-Y-Y-E-G-L-Q-D-K (SEQ ID No. 74)
E-R-X-L-Y-Y-E-G-L-Q-D-K (SEQ ID No. 75)
E-R-R-X-Y-Y-E-G-L-Q-D-K (SEQ ID No. 76)
E-R-R-L-X-Y-E-G-L-Q-D-K (SEQ ID No. 77)
E-R-R-L-Y-X-E-G-L-Q-D-K (SEQ ID No. 78)
E-R-R-L-Y-Y-X-G-L-Q-D-K (SEQ ID No. 79)
E-R-R-L-Y-Y-E-X-L-Q-D-K (SEQ ID No. 80)
E-R-R-L-Y-Y-E-G-X-Q-D-K (SEQ ID No. 81)
E-R-R-L-Y-Y-E-G-L-X-D-K (SEQ ID No. 82)
E-R-R-L-Y-Y-E-G-L-Q-X-K (SEQ ID No. 83)
E-R-R-L-Y-Y-E-G-L-Q-D-X
```

Preferably, the HGS/C constituent oligopeptide is a peptide consisting of any of the following amino acid sequences (wherein X represents an arbitrary amino acid), and having a tumor growth inhibitory effect or a metastasis inhibitory effect:

```
                                       (SEQ ID No. 73)
E-X-R-L-Y-Y-E-G-L-Q-D-K (SEQ ID No. 74)
E-R-X-L-Y-Y-E-G-L-Q-D-K (SEQ ID No. 75)
E-R-R-X-Y-Y-E-G-L-Q-D-K (SEQ ID No. 76)
E-R-R-L-X-Y-E-G-L-Q-D-K (SEQ ID No. 79)
E-R-R-L-Y-Y-E-X-L-Q-D-K (SEQ ID No. 80)
E-R-R-L-Y-Y-E-G-X-Q-D-K (SEQ ID No. 81)
E-R-R-L-Y-Y-E-G-L-X-D-K
```

5. Peptide Preparation

A peptide comprising a part of the C region of HGS (hereinafter referred to as the "peptide of the present invention") can be prepared using a known method, of which the specifics are as follows.

(1) Preparation of Expression Vector

A vector expressing the peptide of the present invention is not limited as long as it is retained in the host cell for expressing it, and examples thereof include plasmid DNA, bacteriophages and the like.

Examples of the plasmid DNA include pME18S, pcDNA3, pBR322, pUC18, pUC19, pUC118, pUC119, and pBluescript, and it may also be other plasmids derived from *Escherichia coli, Bacillus subtilis*, yeast and the like. Examples of the phage DNA include λ phages (Charon 4A, Charon 21A, EMBL3, EMBL4, λgt10, and λgt11).

As a method for incorporating the polynucleotide encoding the peptide of the present invention into a vector, a method of cleaving with an appropriate restriction enzyme and then ligating by the effect of a ligase or the like is adopted (see the above Molecular cloning, CSHL Press, etc.).

For the polynucleotide encoding the peptide of the present invention, for example, it is possible to design a primer for amplifying each polynucleotide in the C region, then amplify the region using a PCR method or the like, followed by ligation of only the desired part to the vector using a restriction enzyme or ligase. In addition, it is also possible to design a primer that amplifies the target part, amplify it by the PCR method, and ligate it to the vector.

(2) Transformation

The host used in the present invention is not limited as long as it expresses the target peptide after the gene encoding the target peptide has been introduced. Examples thereof include, but are not limited to, mammalian cells, bacteria such as bifidobacteria, lactic acid bacteria, and *Escherichia coli*, insect cells, yeast, and fungi.

The recombinant DNA can be introduced into the host by a known method. Examples of the methods for introducing the above vectors into a host include the calcium phosphate method, DEAE-dextran method, electroporation, and cationic lipid method.

In addition, the introduction of DNA can be confirmed using selectable marker genes (for example, ampicillin resistance gene, neomycin resistance gene, hygromycin resistance gene, tetracycline resistance gene, chloramphenicol resistance gene, kanamycin resistance gene, zeocin resistance gene, blasticidin resistance gene, and the like).

(3) Peptide Production

The peptide of the present invention can be obtained by culturing the above transformants comprising the polynucleotide encoding the peptide or a mutant thereof, and collecting the peptide from the culture.

"Culture" means either a culture supernatant, cultured cells, cultured microbial cells, or disrupted cells or microbial cells. The transformant of the present invention can be cultured according to a conventional method used for culturing the host.

When culturing a transformant into which an expression vector with an inducible transcription promoter as a promoter is introduced, an inducer may be added to the medium as needed. The amount of IPTG added when IPTG is used as the inducer is 0.1 to 1.0 mM, which is added 2 to 12 hours after the start of culturing, and the culture is further continued for 1 to 12 hours after the addition.

When the peptide of the present invention is accumulated in the microbial cells or cells after the culture, the target peptide is collected by disrupting the microbial cells or cells by homogenization or the like. When the peptide of the present invention is produced outside of the microbial cells or cells, the culture solution is used as it is, or the microbial cells or cells are removed by centrifugation or the like. Then, the peptide is collected from the culture solution by ammonium sulfate precipitation or the like, and further isolated and purified using various chromatographies and the like as necessary.

In addition, in the present invention, it is possible to produce the peptide of the present invention by using a cell-free protein synthesis system without any living cells.

The cell-free protein synthesis system is a system that synthesizes proteins in an artificial container such as a test tube using a cell extract, and for example, reads mRNA information to synthesize a protein on a ribosome. The cell-free protein synthesis system used in the present invention also includes a cell-free transcription system that synthesizes RNA using DNA as a template.

As the cell extract, an extract derived from eukaryotic cells or prokaryotic cells, for example, an extract of wheat germ, rabbit reticulocytes, mouse L-cells, HeLa cells, CHO cells, budding yeast, *Escherichia coli*, and the like can be used. These cell extracts may be concentrated or may not be concentrated.

In the present invention, cell-free protein synthesis can also be performed using a commercially available kit. Examples of such a kit include the reagent kits PROTEIOS™ (Toyobo) and TNT™ System (Promega), and the synthesizers PG-Mate™ (Toyobo) and RTS (Roche Diagnostics).

The peptide of the present invention obtained by cell-free protein synthesis can be purified by selecting any chromatography as described above. In addition, it is possible to confirm by SDS-PAGE and the like that the peptide of the present invention has been isolated and purified.

Moreover, the peptide of the present invention can also be obtained by cleaving it from full-length HGS or the like with cyanogen bromide, a peptidase or the like. The peptidase is not limited as long as it can cleave the peptide, and examples thereof include trypsin, chymotrypsin, and lysyl endopeptidase.

(4) Peptide Synthesis

The peptide of the present invention can be obtained by chemical synthesis. Peptide synthesis can be carried out by a known method with a synthesizer such as the Model 433A peptide synthesizer (Applied Biosystems) or PSSM-8 (Shimadzu Corporation). In addition, the peptide of the present invention can also be obtained by commissioning the peptide synthesis to a peptide synthesis contractor such as GL Biochem (Shanghai) Ltd or Hayashi Kasei Co., Ltd., and purchasing the peptide. The same applies to the peptides to which a cell penetrating peptide has been added.

6. Antitumor Agent

The peptide of the present invention or a vector expressing the peptide has a tumor growth inhibitory effect and/or a metastasis inhibitory effect. Therefore, a composition comprising these can be used as an antitumor agent. In addition, the peptide of the present invention or a vector expressing the peptide can be used in the manufacture of an antitumor agent or a medicament for treating a cancer or tumor. That is, the present invention provides an antitumor agent comprising the peptide of the present invention or a vector expressing the peptide, and a method for using the peptide of the present invention or a vector expressing the peptide in the manufacture of an antitumor agent or a medicament for treating a cancer or tumor.

Since the antitumor agent of the present invention inhibits only anchorage-independent growth and does not inhibit anchorage-dependent growth, it is presumed not to inhibit normal cell growth. Therefore, it is presumed that the occurrence of side effects associated with the inhibition of normal cell growth is suppressed or hardly occurs with the antitumor agent of the present invention.

That is, the antitumor agent of the present invention remarkably suppresses the growth and metastasis of tumors, while also suppressing the occurrence of side effects, and is therefore extremely useful for the treatment of cancer.

Examples of the "cancer" or "tumor" in the present invention include, but are not limited to, brain tumor, esophageal cancer, tongue cancer, lung cancer, breast cancer, pancreatic cancer, stomach cancer, small intestinal and duodenal cancer, colorectal cancer (colon cancer and rectal cancer), bladder cancer, renal cancer, liver cancer, prostate cancer, uterine cancer, cervical cancer, ovarian cancer, thyroid cancer, gallbladder cancer, pharyngeal cancer, sarcoma (such as osteosarcoma, chondrosarcoma, Kaposi's sarcoma, myosarcoma, angiosarcoma, and fibrosarcoma), and melanoma as solid cancers, and leukemia (for example, chronic myelogenous leukemia (CML), acute myelogenous leukemia (AML), chronic lymphocytic leukemia (CLL), and acute lymphocytic leukemia (ALL)), lymphoma, and multiple myeloma (MM) as hematological tumors.

In addition, "metastasis" in the present invention means that cancer cells are transported to another site away from the primary tumor via the blood or lymphatic system or during surgery to form a new foci there. Alternatively, "metastasis" refers to "the ability of cancer cells to spread and form new foci (i.e., form metastasis) at discrete sites" (Hill, R. P, "Metastasis", The Basic Science of Oncology, Edited by Tannock et al., 178-195 (McGraw-Hill, New York, 1992).

The antitumor agent of the present invention can contain the peptide of the present invention, a vector expressing the peptide, as well as pharmaceutically acceptable carriers. The "pharmaceutically acceptable carrier" refers to any carrier suitable for use as an antitumor agent (liposomes, lipid vesicles, micelles, etc.), diluents, excipients, wetting agents, buffers, suspending agents, lubricants, adjuvants, emulsifiers, disintegrants, absorbers, preservatives, surfactants, colorants, flavoring agents, or sweeteners.

The antitumor agent of the present invention can take the form of injections, lyophilized products, tablets, hard capsules, soft capsules, granules, powders, pills, syrups, suppositories, cataplasms, ointments, creams, eye drops, and the like.

The antitumor agent of the present invention is administered locally or systemically by any means known to those skilled in the art. The dose varies depending on factors such as the subject's age, body weight, health condition, sex, symptoms, route of administration, frequency of administration, and dosage form, and a specific procedure of administration can be set by those skilled in the art. For example, for adults, when the antitumor agent of the present invention is administered as a tablet, 0.1 µg to 10 g, preferably 1 µg to 1 g, more preferably 10 µg to 100 mg can be administered 1 to 5 times a day.

The antitumor agent of the present invention can be administered to mammals. Examples of mammals include mice, rats, hamsters, guinea pigs, rabbits, cats, dogs, goats, pigs, sheep, cows, horses, monkeys, and humans.

Furthermore, when the antitumor agent of the present invention is used as a gene therapy agent, examples of the method for using of the antitumor agent include a method of directly administering the antitumor agent of the present invention by injection, as well as a method of administering a vector carrying a nucleic acid. Examples of the vector include adenoviral vectors, adeno-associated virus vectors, herpesvirus vectors, vaccinia virus vectors, retroviral vectors, and lentiviral vectors, and using these viral vectors allows administering more efficiently.

Moreover, it is also possible to introduce the antitumor agent of the present invention into phospholipid vesicles such as liposomes and administer the vesicles. The vesicles retaining the peptide are introduced into predetermined cells by the lipofection method. Then, the obtained cells are systemically administered, for example, intravenously or intraarterially. They can also be locally administered to the brain and the like. For example, when administering the antitumor agent to an adult, 0.1 µg/kg to 1000 mg/kg per day, preferably 1 µg/kg to 100 mg/kg per day can be administered.

Furthermore, a vector expressing the peptide of the present invention can be transformed into a host such as bifidobacteria, lactic acid bacteria, yeast, and filamentous bacteria, and the transformant can be used as an antitumor agent. Examples of bifidobacteria include *Bifidobacterium longum*, *Bifidobacterium bifidum*, and *Bifidobacterium breve*. Examples of lactic acid bacteria include the genus *Lactobacillus*, the genus *Streptococcus*, the genus *Leuconostoc*, and the genus *Pediococcus*. These transformants can be used as they are, or can be appropriately formulated into the above dosage forms and used as the antitumor agent of the present invention.

7. Tumor Growth Inhibitor and Metastasis Inhibitor

The peptide of the present invention and a vector expressing the peptide have a tumor growth inhibitory effect and a metastasis inhibitory effect. Therefore, a composition comprising these can be used as a tumor growth inhibitor and metastasis inhibitor.

The tumor growth inhibitor and metastasis inhibitor of the present invention can be used as a reagent or for the treatment of mammals, and the administration form, additives, route of administration, target of administration, dose, and the like can be appropriately selected by those skilled in the art according to the description in "6. Antitumor agent".

8. Method for Treating Cancer or Tumor and Use in the Method

The peptide of the present invention and a vector expressing the peptide have a tumor growth inhibitory effect and a metastasis inhibitory effect. Therefore, these peptides and vectors can be used in methods for treating a cancer or tumor. That is, the present invention provides a method for treating a cancer or tumor in a subject in need of treatment for a cancer or tumor, which comprises administering a therapeutically effective amount of the peptide of the present invention and a vector expressing the peptide to the subject. In addition, the present invention provides a use of the peptide of the present invention and a vector expressing the peptide in the treatment of a cancer or tumor.

In the method of the present invention, the administration form, additives, route of administration, target of administration, dose, and the like of the peptide of the present invention and a vector expressing the peptide can be appropriately selected by those skilled in the art according to the description in "6. Antitumor agent".

9. Method for Inhibiting the Growth or Metastasis of Cancer or Tumor, and Use in the Method The peptide of the present invention and a vector expressing the peptide have a tumor growth inhibitory effect and a metastasis inhibitory effect. Therefore, these peptides and vectors can be used in a method for inhibiting the growth or metastasis of a cancer or tumor. That is, the present invention provides a method for inhibiting the growth or metastasis of a cancer or tumor in a subject in need of inhibiting the growth or metastasis of a cancer or tumor, which comprises administering an effective amount of the peptide of the present invention and a vector expressing the peptide to the subject. In addition, the present invention provides the peptide of the present invention and a vector expressing the peptide for use in the treatment of a cancer or tumor.

In the method of the present invention, the administration form, additives, route of administration, target of administration, dose, and the like of the peptide of the present invention and a vector expressing the peptide can be appropriately selected by those skilled in the art according to the description in "6. Antitumor agent".

Hereafter, the present invention is described in detail with examples, but the present invention is not limited to these examples.

Example 1

Preparation and Screening of HGS/C Constituent Oligopeptide Library

1. Preparation of HGS/C Constituent Oligopeptide Library

A library of oligopeptides comprising 10 consecutive amino acid residues of the amino acid sequence of the C region of HGS was synthesized. The inventor designed the amino acid sequences of the oligopeptides comprised in the library, and GL Biochem (Shanghai) Ltd. was commissioned to synthesize the oligopeptides.

The oligopeptides comprised in this library have a length of 10 amino acid residues, and have the sequences of the amino acid sequence of the C region of HGS shifted by 1 amino acid each in order from the N-terminus toward the C-terminus, that is, sequences overlapping each other by 9 amino acid residues, thereby covering the amino acid sequence of HGS/C. For example, the oligopeptides comprised in this library having at the N-terminus the amino acid residues of positions 460 to 470, 503 to 511 and 523 to 532 from the N-terminus of the entire length of HGS are as shown in the table below.

TABLE 5

| Code name | Amino acid sequence | SEQ ID NO |
|---|---|---|
| OP10-460 | LDERRLYYEG | 35 |
| OP10-461 | DERRLYYEGL | 36 |
| OP10-462 | ERRLYYEGLQ | 37 |
| OP10-463 | RRLYYEGLQD | 38 |
| OP10-464 | RLYYEGLQDK | 39 |
| OP10-465 | LYYEGLQDKL | 40 |
| OP10-466 | YYEGLQDKLA | 41 |
| OP10-467 | YEGLQDKLAQ | 42 |
| OP10-468 | EGLQDKLAQI | 43 |
| OP10-469 | GLQDKLAQIR | 44 |
| OP10-470 | LQDKLAQIRD | 45 |
| . . . | | |

TABLE 5-continued

| Code name | Amino acid sequence | SEQ ID NO |
|---|---|---|
| OP10-503 | ERQRQIQLAQ | 46 |
| OP10-504 | RQRQIQLAQK | 47 |
| OP10-505 | QRQIQLAQKL | 48 |
| OP10-506 | RQIQLAQKLE | 49 |
| OP10-507 | QIQLAQKLEI | 50 |
| OP10-508 | IQLAQKLEIM | 51 |
| OP10-509 | QLAQKLEIMR | 52 |
| OP10-510 | LAQKLEIMRQ | 53 |
| OP10-511 | AQKLEIMRQK | 54 |
| . . . | | |
| OP10-523 | EYLEVQRQLA | 55 |
| OP10-524 | YLEVQRQLAI | 56 |
| OP10-525 | LEVQRQLAIQ | 57 |
| OP10-526 | EVQRQLAIQR | 58 |
| OP10-527 | VQRQLAIQRL | 59 |
| OP10-528 | QRQLAIQRLQ | 60 |
| OP10-529 | RQLAIQRLQE | 61 |
| OP10-530 | QLAIQRLQEQ | 62 |
| OP10-531 | LAIQRLQEQE | 63 |
| OP10-532 | AIQRLQEQEK | 64 |

2. Screening Based on Surface Plasmon Resonance (SPR) Analysis

From the library of HGS/C constituent oligopeptides synthesized above, the oligopeptides having strong interactions with HGS and STAM were screened using surface plasmon resonance (SPR) analysis.

Specifically, Glutathione S-transferase (GST)-labeled HGS (Human) Recombinant Protein (Abnova), GST-labeled STAM (Human) Recombinant Protein (Abnova), or GST (Abnova) was immobilized on a ProteOn™ GLH sensor chip.

The interactions between the HGS/C constituent oligopeptides and these immobilized proteins were measured using the ProteOn™ XPR36 interaction array system (Bio-Rad). Using the GST value as a blank value, the dissociation rate constants (Kd) of the HGS/C-constituent oligopeptides with each of GST-labeled HGS and GST-labeled STAM were measured. Then, the oligopeptides having a strong interaction with both HGS and STAM proteins were searched using the dissociation rate constant as an index.

As a result, OP10-463, OP10-507 and OP10-527 were selected as oligopeptides having a strong interaction with both HGS and STAM proteins.

In addition, the oligopeptide in which one amino acid residue (that is, glutamic acid (E) and lysine (K)) was added at the end and front of OP10-463, that is, OP12-462 was synthesized as an oligopeptide with enhanced interaction with HGS and STAM. Similarly, examples of 12 amino acid residue-long oligopeptides to which amino acid residues were added include those listed in the table below.

TABLE 6

| Code name | Amino acid sequence | SEQ ID NO |
|---|---|---|
| OP12-460 | LDERRLYYEGLQ | 65 |
| OP12-461 | DERRLYYEGLQD | 66 |
| OP12-462 | ERRLYYEGLQDK | 67 |
| OP12-463 | RRLYYEGLQDKL | 68 |
| OP12-464 | RLYYEGLQDKLA | 69 |
| OP12-465 | LYYEGLQDKLAQ | 70 |
| OP12-466 | YYEGLQDKLAQI | 71 |

OP12-462, OP10-507 and OP10-527 were used in the following tests as representative examples of the selected oligopeptides and the oligopeptides obtained by adding amino acids to the selected oligopeptides.

Example 2

1. Evaluation of Activity of HGS/C Constituent Oligopeptides of the Present Invention (1) In Vitro Anchorage-Independent/Dependent Growth Inhibition Test Cancer cells proliferate in an anchorage-independent manner, and normal cells proliferate in an anchorage-dependent manner. Therefore, if the tested oligopeptide inhibits only anchorage-independent growth and does not inhibit anchorage-dependent growth, it means that the oligopeptide inhibits only the growth of cancer cells and does not inhibit the growth of normal cells.

In the present example, the Ultra-Low Attachment Surface Corning Costar 96 Well Cell Culture Plate 3474 (Corning) was used as an Ultra-Low Attachment Surface (ULAS) plate, and Tissue Culture Treated Corning Costar 96 Well Cell Culture Plate 3595 (Corning) was used as a normal plate.

As cells, mouse melanoma B16 cells and human colorectal cancer-derived COLO 205 cells were used, and Cell Counting Kit-8 (Dojindo Laboratories) was used to evaluate cell growth.

B16 cells or COLO 205 cells (2E+3 cells/0.2 ml Opti-MEM medium, 5% FBS/well) were seeded in each well of the ULAS plate and normal plate. The test oligopeptides (OP12-462, OP10-507 and OP10-527) (0, 0.16, 0.4, 8 nmol) were each added and cultured at 37° C.

After 7 days, 0.1 ml of Cell Counting Kit-8 solution (5-fold PBS diluted solution) was added, and the absorbance A450 nm was immediately measured and set as the T0 blank value.

After incubating at 37° C. for 2 hours, the absorbance A450 nm was measured again and set as T2. The change=T2−T0 was defined as the anchorage-independent growth activity value or the anchorage-dependent growth activity value. The cell growth activity when adding a test oligopeptide was quantified as the relative ratio to the cell growth activity when no test oligopeptide was added.

The results are shown in FIGS. 2A and 2B. As is clear from these figures, OP12-462, OP10-507 and OP10-527 strongly inhibited the anchorage-independent growth activity of mouse melanoma B16 cells (FIG. 2A) and human colorectal cancer-derived COLO 205 cells (FIG. 2B) in a concentration-dependent manner. On the other hand, these oligopeptides did not inhibit at all or hardly inhibited the anchorage-dependent growth activity of both cells. That is, it was shown that while OP12-462, OP10-507 and OP10-527 remarkably inhibit the growth of cancer or tumor cells, they do not inhibit the growth of normal cells.

These results show that the antitumor agent comprising the peptide of the present invention can remarkably inhibit the side effects associated with the inhibition of the growth of normal cells, while remarkably inhibiting the growth of cancer or tumor cells.

(2) In Vivo Xenograft Test

COLO 205 cells (1E+6 cells/0.2 ml PBS) were inoculated subcutaneously into the back of BALB/c Slc-nu/nu nude mice (female) (n=5 or 6). The day after 10 days was set as Day 0, and PBS or the test oligopeptides (OP12-462, OP10-507 and OP10-527) (5 mg/kg body weight) was administered as a 0.2 ml PBS solution in the tail vein once daily for 10 days from Day 0 to Day 9. The size of the tumor formed was measured once daily from Day 0. The tumor volume was estimated by measuring the minor axis and major axis of the tumor (tumor volume=(semi-minor axis×semi-minor axis×semi-major axis×$\pi$)/6).

As a result, OP12-462, OP10-507 and OP10-527 all statistically significantly inhibited the tumor growth of COLO 205 cells (FIGS. 3A to 3C). Furthermore, these oligopeptides all remarkably inhibited tumor growth as compared with the conventional oligopeptides used in the Comparative Example described later (Comparative Example, FIGS. 6A to 6C).

These results show that the oligopeptide of the present invention is a peptide having a remarkably high tumor growth inhibitory effect as compared with conventional HGS/C constituent oligopeptides. In addition, as described above, it was shown that since the oligopeptides of the present invention do not inhibit the growth of normal cells, the antitumor agents comprising these oligopeptides are extremely useful as an antitumor agent capable of inhibiting the occurrence of side effects while exerting a remarkable tumor growth inhibitory effect.

(3) Experimental Lung Metastasis Inhibition Test

The metastasis inhibitory effect of OP12-462 on the experimental lung metastasizing ability of mouse melanoma B16 cells was examined.

First, a PBS solution (0.2 ml PBS) of mouse melanoma B16 cells (1E+5 cells) and the test oligopeptide (OP12-462) (40 nmol) was incubated at 37° C. for 2 hours. After incubation, this solution was administered to C57BL/6 mice (female) in the tail vein. The number of B16 cell metastatic tumor colonies in the mouse lung was counted 28 days after the tail vein administration of B16 cells. The ability of the oligopeptide OP12-462 to inhibit metastasis was quantified as the relative ratio of the number of the tumor colonies treated with the oligopeptide to the number of tumor colonies of B16 cells untreated with the oligopeptide.

As a result, OP12-462 remarkably inhibited the experimental lung metastasizing ability of mouse melanoma B16 cells (FIG. 4). In FIG. 4, "vehicle" represents the sample untreated with the oligopeptide.

These results show that the oligopeptide of the present invention has a remarkable metastasis inhibitory effect. Furthermore, it was also shown that the antitumor agent comprising the oligopeptide of the present invention is useful as a metastasis inhibitor.

2. Preparation of Alanine Substituted Peptide of HGS/C Constituent Oligopeptide and Evaluation of its Activity
(1) Synthesis of Alanine Substituted Peptide of HGS/C Constituent Oligopeptide OP12-462 substituted peptides in which one amino acid residue of the oligopeptide OP12-462 is substituted with alanine were synthesized.

The oligopeptide in which the Nth residue from the NH2 terminus is substituted with alanine was defined as OP12-462-AN, and OP12-462-A1 to OP12-462-A12 were synthesized. The synthesized oligopeptides are shown in the table below.

TABLE 7

| Code name | Amino acid sequence | SEQ ID NO |
|---|---|---|
| OP12-462 | ERRLYYEGLQDK | 67 |
| OP12-462-A1 | ARRLYYEGLQDK | 84 |
| OP12-462-A2 | EARLYYEGLQDK | 85 |
| OP12-462-A3 | ERALYYEGLQDK | 86 |
| OP12-462-A4 | ERRAYYEGLQDK | 87 |
| OP12-462-A5 | ERRLAYEGLQDK | 88 |
| OP12-462-A6 | ERRLYAEGLQDK | 89 |
| OP12-462-A7 | ERRLYYAGLQDK | 90 |
| OP12-462-A8 | ERRLYYEALQDK | 91 |
| OP12-462-A9 | ERRLYYEGAQDK | 92 |
| OP12-462-A10 | ERRLYYEGLADK | 93 |
| OP12-462-A11 | ERRLYYEGLQAK | 94 |
| OP12-462-A12 | ERRLYYEGLQDA | 95 |

(2) In Vitro Anchorage-Independent Growth Inhibition Test

As was in the above "1. (1)", an in vitro anchorage-independent growth inhibition test was conducted on the oligopeptide OP12-462 and the OP12-462 alanine substituted peptides.

As a result, all OP12-462 alanine substituted peptides remarkably inhibited in vitro anchorage-independent growth as compared with the sample untreated with an oligopeptide (vehicle) (FIG. 5).

This result shows that an oligopeptide consisting of an amino acid sequence in which one amino acid is mutated in the amino acid sequence of OP12-462 has a tumor growth inhibitory effect. Similarly, it was also shown that the oligopeptides having 90% or more sequence identity with OP12-462 have a tumor growth inhibitory effect.

Furthermore, the OP12-462 alanine substituted peptide, OP12-462-A3, inhibited in vitro anchorage-independent growth equally to or more than OP12-462, thus showing that the amino acid at position 3 of the amino acid sequence of OP12-462 can be any amino acid. That is, it was shown that an oligopeptide consisting of the amino acid sequence E-R-X-L-Y-Y-E-G-L-Q-D-K (wherein X represents an arbitrary amino acid) (SEQ ID NO: 74) also has a tumor growth inhibitory effect.

(3) Experimental Lung Metastasis Inhibition Test

As was in the above "1. (3)", an experimental lung metastasis inhibition test was conducted on the oligopeptide OP12-462 and the OP12-462 alanine substituted peptides.

As a result, OP12-462 remarkably inhibited the experimental lung metastasizing ability of mouse melanoma B16 cells. In addition, the OP12-462 alanine substituted peptides, OP12-462-A3, OP12-462-A4 and OP12-462-A9, also remarkably inhibited the experimental lung metastasizing ability as compared with the sample untreated with an oligopeptide (vehicle).

This result shows that the ability to inhibit metastasis can be maintained even with a peptide in which the amino acid at the position 3, 4 or 9 of the amino acid sequence of OP12-462 is substituted with any amino acid. That is, it was shown that the oligopeptide consisting of the amino acid sequence E-R-X-L-Y-Y-E-G-L-Q-D-K, E-R-R-X-Y-Y-E-G-L-Q-D-K or E-R-R-L-Y-Y-E-G-X-Q-D-K (wherein X represents an arbitrary amino acid) (SEQ ID NO: 74, 75 or 80) has a metastasis inhibitory effect.

Comparative Example

Evaluation of Activity of Conventional HGS/C Constituent Oligopeptides
In Vivo Xenograft Test With the same method as in the above "[Example 2] 1. (2)", the tumor growth inhibitory ability was evaluated for OP10-7, OP10-10 and OP10-11, which are typical examples of conventional HGS/C constituent oligopeptides.

As a result, while a tumor growth inhibitory effect was observed (FIGS. 6A to 6C), the effect was remarkably lower than that of OP12-462, OP10-507 and OP10-527 of the present invention.

That is, it was shown that the HGS/C constituent oligopeptides of the present invention (OP12-462, OP10-507 and OP10-527) are peptides having a remarkably high tumor growth inhibitory effect as compared with conventional HGS/C constituent oligopeptides.

INDUSTRIAL APPLICABILITY

According to the present invention, it is possible to provide a peptide having a higher tumor growth inhibitory effect as compared with conventional partial peptides of HGS/C, and an antitumor agent comprising the same.
[Sequence Listing Free Text]
  SEQ ID NOs: 13-95: a synthesized peptide

The invention claimed is:

1. A method for inhibiting growth or metastasis of a solid cancer in a subject, which comprises administering a therapeutically effective amount of a peptide to the subject having a solid cancer, wherein the peptide is the following (a) or (b):
 (a) a peptide consisting of the amino acid sequence of SEQ ID NO: 67; or
 (b) a peptide having 90% or more sequence identity with the peptide consisting of the amino acid sequence of SEQ ID NO: 67, and having a tumor growth inhibitory effect or a metastasis inhibitory effect.

2. A method for treating a solid cancer in a subject, which comprises administering a therapeutically effective amount of a peptide to the subject having a solid cancer, wherein the peptide is the following (a) or (b):
 (a) a peptide consisting of the amino acid sequence of SEQ ID NO: 67; or
 (b) a peptide having 90% or more sequence identity with the peptide consisting of the amino acid sequence of SEQ ID NO: 67, and having a tumor growth inhibitory effect or a metastasis inhibitory effect.

3. The method according to claim 2, wherein the peptide is a peptide consisting of any of the following amino acid sequences (j) to (p), wherein X is any amino acid, and having a tumor growth inhibitory effect or a metastasis inhibitory effect:

```
                                              (SEQ ID No. 73)
(j) E-X-R-L-Y-Y-E-G-L-Q-D-K, (SEQ ID No. 74)
(k) E-R-X-L-Y-Y-E-G-L-Q-D-K, (SEQ ID No. 75)
(l) E-R-R-X-Y-Y-E-G-L-Q-D-K, (SEQ ID No. 76)
(m) E-R-R-L-X-Y-E-G-L-Q-D-K, (SEQ ID No. 79)
(n) E-R-R-L-Y-Y-E-X-L-Q-D-K, (SEQ ID No. 80)
(o) E-R-R-L-Y-Y-E-G-X-Q-D-K,
and (SEQ ID No. 81)
(p) E-R-R-L-Y-Y-E-G-L-X-D-K.
```

4. The method according to claim 2, wherein the peptide consists of the amino acid sequence of SEQ ID NO: 67.

5. The method according to claim 2, wherein the solid cancer is colorectal cancer.

6. The method according to claim 2, wherein the peptide consists of the amino acid sequence of SEQ ID NO: 67 and wherein the solid cancer is colorectal cancer.

* * * * *